US010918641B2

(12) United States Patent
Esther, Jr. et al.

(10) Patent No.: US 10,918,641 B2
(45) Date of Patent: Feb. 16, 2021

(54) USE OF MTAP INHIBITORS FOR THE TREATMENT OF LUNG DISEASE

(71) Applicants: The University of North Carolina at Chapel Hill, Chapel Hill, NC (US); Albert Einstein College of Medicine, Inc., Bronx, NY (US); Victoria Link Limited, Wellington (NZ)

(72) Inventors: Charles R. Esther, Jr., Chapel Hill, NC (US); Michael R. Knowles, Chapel Hill, NC (US); Wanda Kay O'Neal, Cary, NC (US); Deepika Polineni, Kansas City, MI (US); Steven Isaacman, Oak Beach, NY (US); Andrew B. Mahon, New York, NY (US)

(73) Assignees: The University of North Carolina at Chapel Hill, Chapel Hill, NC (US); Albert Einstein College of Medicine, Inc., Bronx, NY (US); Victoria Link Limited, Wellington (NZ)

( * ) Notice: Subject to any disclaimer, the term of this patent is extended or adjusted under 35 U.S.C. 154(b) by 47 days.

(21) Appl. No.: 15/943,964

(22) Filed: Apr. 3, 2018

(65) Prior Publication Data

US 2018/0353511 A1    Dec. 13, 2018

Related U.S. Application Data

(63) Continuation of application No. PCT/US2016/055444, filed on Oct. 5, 2016.

(60) Provisional application No. 62/237,097, filed on Oct. 5, 2015.

(51) Int. Cl.
| | | |
|---|---|---|
| A61K 31/519 | (2006.01) |
| A61P 11/00 | (2006.01) |
| A61P 29/00 | (2006.01) |
| A61K 45/06 | (2006.01) |
| C07D 487/04 | (2006.01) |
| A61K 9/00 | (2006.01) |

(52) U.S. Cl.
CPC .......... *A61K 31/519* (2013.01); *A61K 9/0019* (2013.01); *A61K 9/0043* (2013.01); *A61K 9/0053* (2013.01); *A61K 45/06* (2013.01); *A61P 11/00* (2018.01); *A61P 29/00* (2018.01); *C07D 487/04* (2013.01)

(58) Field of Classification Search
CPC .. A61K 31/519; A61K 9/0019; A61K 9/0043; A61K 9/0053; A61K 45/05; A61P 11/00; A61P 29/00; C07D 487/04
USPC ...................................................... 514/210.02
See application file for complete search history.

(56) References Cited

U.S. PATENT DOCUMENTS

| | | | |
|---|---|---|---|
| 7,034,007 B1 | 4/2006 | Nyce et al. | |
| 2010/0222370 A1* | 9/2010 | Schramm | A61K 31/519 514/265.1 |
| 2015/0274741 A1* | 10/2015 | Evans | C07D 487/04 514/265.1 |

FOREIGN PATENT DOCUMENTS

WO    2006014913 A2    2/2006

OTHER PUBLICATIONS

Conway et al American Journal of Respiratory and critical care Medicine, 2016, 193(2) 116-130) (Year: 2016).*
Guan et al. "Methylthioinosine Phosphorylase from Pseudomonas aeruginosa. Structure and Annotation of a Novel Enzyme in Quorum Sensing", Biochemistry 50(7): 1247-1254 (2011).
Smith et al. "The Pseudomonas aeruginosa Quorum-Sensing Molecule N-(3-Oxododecanoyl)Homoserine Lactone Contributes to Virulence and Induces Inflammation in Vivo", Journal of Bacteriology 184(4):1132-1139 (2002).
Notification of Transmittal of the International Search Report and the Written Opinion of the International Searching Authority, or the Declaration corresponding to International Application No. PCT/US2016/055444 dated Dec. 22, 2016.
Notification Concerning Transmittal of International Preliminary Report on Patentability corresponding to International Application No. PCT/US2016/055444 dated Apr. 19, 2018.

* cited by examiner

*Primary Examiner* — Yevgeny Valenrod
(74) *Attorney, Agent, or Firm* — Myers Bigel, P.A.

(57) ABSTRACT

This invention relates generally to the use of 5'-methylthioadenosine phosphorylase (MTAP) inhibitors for the treatment of lung diseases associated with inflammation, such as cystic fibrosis (CF) and chronic obstructive pulmonary disease (COPD). Small molecule inhibitors of MTAP can sustain accumulation of endogenous MTA to therapeutically beneficial levels resulting in decreased inflammation in CF and COPD.

21 Claims, 8 Drawing Sheets

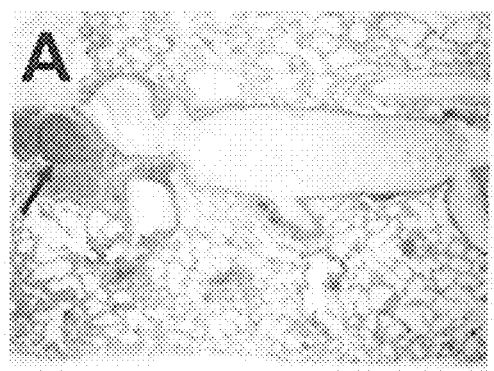
FIG. 9A
FIG. 9C
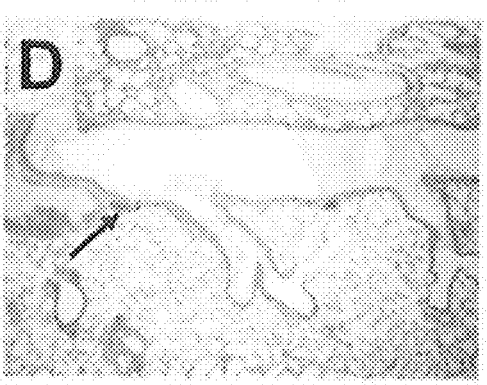
FIG. 9B
FIG. 9D
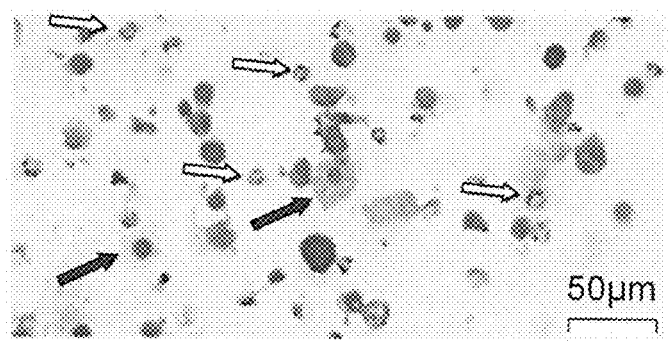
FIG. 10A
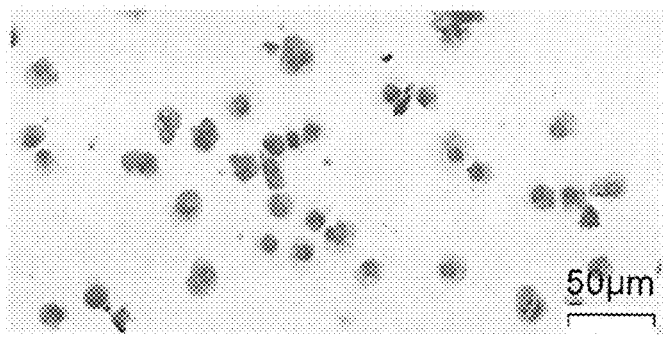
FIG. 10B

USE OF MTAP INHIBITORS FOR THE TREATMENT OF LUNG DISEASE

CROSS-RELATED APPLICATIONS

This application is a continuation of and claims priority to International Patent Application No. PCT/US2016/055444, filed Oct. 5, 2016, which claims priority under 35 U.S.C. § 119(e) to U.S. Provisional Patent Application No. 62/237,097, filed on Oct. 5, 2015, the contents of each of which are incorporated herein by reference in their entirety.

FIELD OF THE INVENTION

This invention relates generally to the use of 5'-methylthioadenosine phosphorylase (MTAP) inhibitors for the treatment of lung diseases associated with inflammation, such as cystic fibrosis and chronic obstructive pulmonary disease.

BACKGROUND OF THE INVENTION

CF is a global health issue that affects over 70,000 people worldwide, including ~30,000 Americans. A defect in the cystic fibrosis transmembrane conductance regulator (CFTR) gene is manifested clinically in the airways of patients, where functional defects in host antibacterial-defense mechanisms permit early colonization and infection. Infection induces a sustained and intense inflammatory response that is observed locally in the airways. Chronic obstructive pulmonary disease (COPD) is recognized as an inflammatory disease and inflammation intensity is a key factor in the severity of COPD. Lung disease is the primary cause of morbidity and mortality in cystic fibrosis (CF) and COPD patients. Due to the importance of inflammatory response in both CF and COPD lung disease, many forms of anti-inflammatory therapy are being actively pursued, but few have achieved widespread clinical success. The only anti-inflammatory drug to reach the clinic for CF is an anti-bacterial agent with anti-inflammatory properties. Novel therapies which reduce chronic airways inflammation but do not compromise host defense are needed.

Metabolomics studies with human clinical samples and Genome Wide Association Studies (GWAS) demonstrate a genetic and biochemical correlation between increased flux through the methionine (Met) salvage pathway, inflammation, and lung disease severity. Increased Met salvage flux leads to reduced 5'-methylthioadenosine (MTA) metabolite concentrations and increased polyamine levels. The APIP gene was first identified as a protein that interacts with apoptotic protease activating factor Apaf-1 (APIP=Apaf-1 Interacting Protein), and increased expression of APIP inhibits both apoptotic and pyroptotic cell death induced by stimuli such as hypoxia and cytotoxic drugs. Interestingly, further studies demonstrated that APIP encodes 5-methylthioribulose-1-phosphate dehydratase, an enzyme involved in the methionine salvage pathway. This pathway serves to salvage the metabolite MTA generated during synthesis of polyamines (putrescine, spermidine and spermine) and convert it back to methionine. Therefore, increasing APIP expression decreases concentrations of MTA. MTA has a significant regulatory role in inflammatory responses, and the inverse relationship between APIP gene expression and MTA concentrations appears to underlie the APIP mediated regulation of pyroptosis. MTA also acts as a negative regulator of the enzyme ornithine decarboxylase (ODC), the rate-limiting step in synthesis of polyamines. Polyamines have been reported to increase airway mucin secretion and aggregation, providing a potential mechanism for enhancing lung disease. Overall, these findings are congruent with genomic data since they suggest that increased flux through the methionine salvage pathway—as would be expected with increased APIP expression-would inhibit apoptotic responses, reduce MTA levels, and increase polyamine synthesis; all of which would be expected to lead to a more pro-inflammatory phenotype. The anti-inflammatory profile of MTA has been investigated in several preclinical models, where exogenous MTA has been shown to modulate the expression of inflammatory mediators and promote an anti-inflammatory state. Metabolomics studies provide further evidence that increased activity of the methionine salvage pathway is present in CF and associated with lung disease. Mass spectrometric (MS) metabolomics identified metabolites associated with neutrophilic airway inflammation in bronchoalveolar lavage fluid (BALF) from children with CF. In other studies, several polyamines including spermine, spermidine, and putrescine were positively correlated with BALF neutrophil counts, as was adenine (a product of MTA hydrolysis). Although adenine is also a component of adenyl purines, free adenine is not generated in the major pathways of purine metabolism and is specific to the methionine salvage pathway. Spermine and adenine are also elevated in samples with pathogens identified on BALF culture, and spermine is inversely correlated with lung function. These findings demonstrate that metabolites reflective of increased activity of the methionine salvage pathway are also increased in airways inflammation, further supporting a role for this pathway in progression of airways disease.

The present invention addresses previous shortcomings in the art by providing methods for treating and preventing lung inflammation and disorders associated with lung inflammation.

SUMMARY OF THE INVENTION

The present invention provides a new approach to treat airway inflammation in lung diseases such as CF and COPD by blocking MTA metabolism with a small molecule transition state inhibitor of MTAP. Accordingly, in one aspect the invention relates to a method of inhibiting MTA metabolism in the lungs of a subject, comprising administering to the subject an effective amount of a transition state MTAP inhibitor, thereby inhibiting MTA metabolism in the lungs of the subject.

Another aspect the invention relates to a method of increasing levels of endogenous MTA in the lungs of a subject, comprising administering to the subject an effective amount of a transition state MTAP inhibitor, thereby increasing levels of MTA in the lungs of the subject.

A further aspect the invention relates to a method of inhibiting polyamine synthesis in the lungs of a subject, comprising administering to the subject an effective amount of a transition state MTAP inhibitor, thereby inhibiting polyamine synthesis in the lungs of the subject.

An additional aspect the invention relates to a method of inhibiting inflammation in the lungs of a subject, comprising administering to the subject an effective amount of a transition state MTAP inhibitor, thereby inhibiting lung inflammation in the subject.

Another aspect the invention relates to a method of treating a lung disease associated with inflammation (e.g., CF, COPD, or other airway inflammatory diseases) in a subject in need thereof, comprising administering to the subject a therapeutically effective amount of a transition state MTAP inhibitor, thereby treating the lung disease associated with inflammation in the subject.

These and other aspects of the invention are set forth in more detail in the description of the invention below.

BRIEF DESCRIPTION OF THE DRAWINGS

FIGS. 9A-9D show lung histology. Scnn1b-Tg mice develop increased bronchus-associated lymphoid tissue (BALT), as observed in the vehicle treated animals (A, B). BALT was greatly reduced in Scnn1b-Tg mice treated with MTDIA for 3 days (C, D).

FIGS. 10A-10B show airway inflammatory cells. A) Cytospins of BALF from untreated Scnn1b-Tg mice demonstrate the characteristic neutrophils (white arrows) and enlarged macrophages (black arrows) that resolve to a more WT appearance after 3 days of MTDIA treatment (B).

DETAILED DESCRIPTION OF THE INVENTION

Figure 1:
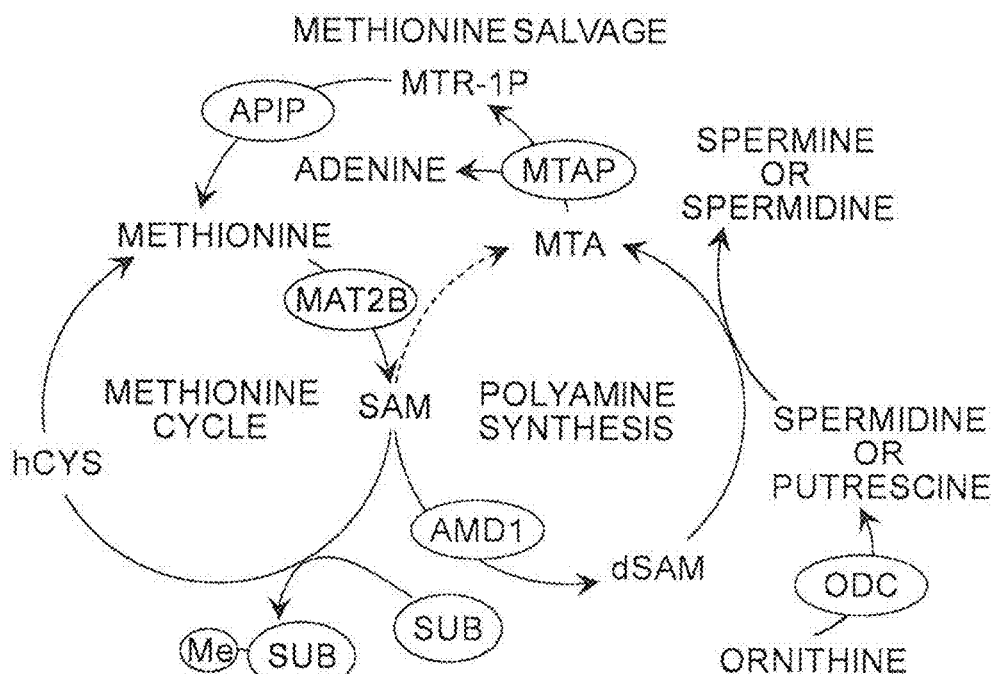
FIG. 1 shows the metabolites and enzymes related to the methionine salvage pathway. APIP, putrescine, spermidine, and spermine are pro-inflammatory, MTA is anti-inflammatory.
Figure 2A:
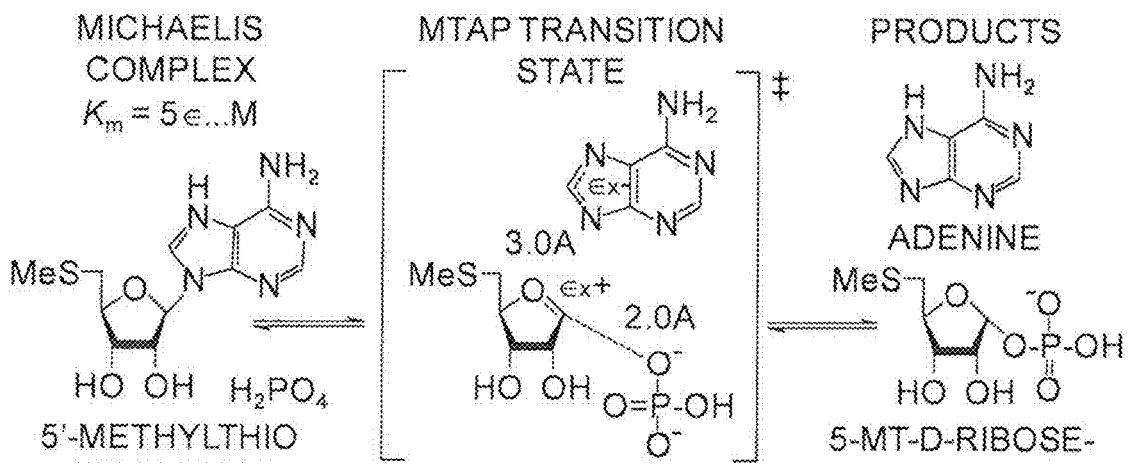
FIGS. 2A-2B show A) phosphorolysis of 5'-methyltyhio-adenosine by human MTAP and the proposed transition state. B) methylthio-DADMe-Immucillin-A (MTDIA) is a powerful inhibitor of human MTAP and the phosphate salt is being advanced towards clinical evaluation.
Figure 2B:
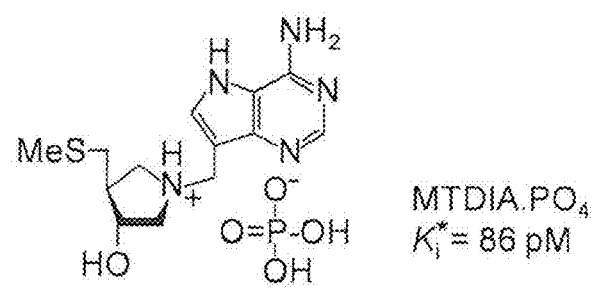

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, +1%, +0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, and those that do not materially affect the basic and novel characteristic(s) of the claimed invention.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

The term "alkyl" means a saturated $C_1$-$C_{30}$ (e.g., $C_1$-$C_{10}$ or $C_1$-$C_5$) aliphatic hydrocarbon, or a partially unsaturated aliphatic hydrocarbon, either branched straight-chained. Examples of alkyl groups include methyl, ethyl, propyl, isopropyl, butyl, isobutyl, tert-butyl, and the like.

The term "alkenyl" means an alkyl group containing at least one double bond.

The term "alkynyl" means an alkyl group containing at least one triple bond.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The term "cycloalkyl" denotes a monocyclic saturated carbocyclic group containing 3-8 carbon atoms, e.g., 3-6 carbon atoms. Examples of cycloalkyl groups include cyclopropyl, cyclobutyl, cyclopentyl, cyclohexyl, cycloheptyl, cyclooctyl, and the like.

The term "alkoxy" denotes an oxygen linked to an alkyl or substituted alkyl as defined above.

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to an aromatic 5-8 membered monocyclic or 8-12 membered bicyclic ring system wherein 0, 1, 2, or 3 atoms of each ring can be substituted by a substituent. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The term "heteroaryl" refers to an aromatic 5-8 membered monocyclic or 8-12 membered bicyclic ring system comprising 1-3 heteroatoms if monocyclic or 1-6 heteroatoms if bicyclic, said heteroatoms selected from O, N, or S, wherein 0, 1, 2 or 3 atoms of each ring can be substituted by a substituent. The term also includes aromatic bicyclic ring systems in which a hydrogen atom has been added to one, two, or three of the ring carbons in one of the rings (e.g., a partially saturated ring).

Examples of heteroaryl groups include pyridyl, furyl or furanyl, benzofuranyl, imidazolyl, benzimidazolyl, pyrimidinyl, thiophenyl or thienyl, benzothiophenyl, quinolinyl, isoquinolinyl, dihydroquinolinyl, dihydroisoquinolinyl, naphthyridinyl, dihydronaphthyridinyl, quinazolinyl, indolyl, indazolyl, thiazolyl, benzothiazolyl, oxazinyl, benzoxazinyl, oxazolyl, benzooxazolyl, dihydrobenzodioxinyl, and the like.

Suitable substituents for aryl and heteroaryl groups are the same as the substituents for alkyl groups.

The term "aralkyl" refers to an aryl or substituted aryl linked to an alkyl or substituted alkyl as defined above.

The term "aralkenyl" refers to an aryl or substituted aryl linked to an alkenyl or substituted alkenyl as defined above.

The term "aralkynyl" refers to an aryl or substituted aryl linked to an alkynyl or substituted alkynyl as defined above.

The term "thiol" refers to SH.

The term "alkylthio" refers to a sulfur linked to an alkyl or substituted alkyl as defined above.

The term "arylthio" refers to a sulfur linked to an aryl or substituted aryl as defined above.

The term "aralkylthio" refers to a sulfur linked to an aralkyl or substituted aralkyl as defined above.

The term "hydroxy" refers to OH.

The term "carboxylic acid" refers to COOH.

The term "carboxylate alkyl ester" refers to COOR wherein R is alkyl.

The term "amino" refers to $NH_2$.

The term "nitro" refers to $NO_2$.

The term "cyano" refers to CN.

The term "thiazole" refers to a 5-member ring comprising a sulfur and a nitrogen.

Figure 3:
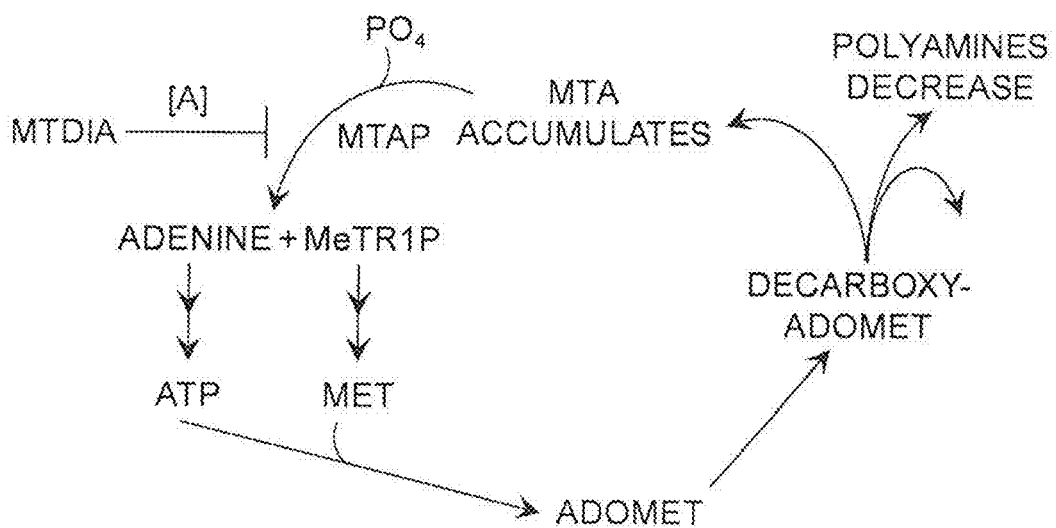
FIG. 3 shows that MTAP is the sole enzyme that metabolizes MTA. A single dose of MTDIA causes the systemic inhibition of MTAP [A] and whole-body accumulation of MTA.

The present invention provides a new approach to treat inflammation in lung disease (e.g., CF and COPD) by blocking MTA metabolism with a small molecule transition state inhibitor of MTAP. The use of MTA alone as a therapeutic for CF has limited utility because of pharmacokinetics (PK). MTAP rapidly metabolizes MTA in vivo with excess MTA cleared renally, as demonstrated by high urine concentrations of MTA in exploratory PK experiments. MTDIA blocks MTA metabolism at MTAP, which causes whole-body accumulation of MTA and simultaneous disruption of polyamine synthesis (FIG. 3). MTDIA inhibits MTAP, the sole enzyme responsible for MTA recycling, with picomolar affinity and a high level of specificity. An oral or i.p. dose of MTDIA inhibits MTAP activity in vivo for >24 h, causes MTA accumulation in plasma to >100-fold higher than baseline levels (FIG. 7A), and ~2-fold decrease in polyamine concentrations.

Accordingly, in one aspect the invention relates to a method of inhibiting MTA metabolism in the lungs of a subject, comprising administering to the subject an effective amount of a transition state MTAP inhibitor, thereby inhibiting MTA metabolism in the lungs of the subject.

Another aspect the invention relates to a method of increasing levels of endogenous MTA in the lungs of a subject, comprising administering to the subject an effective amount of a transition state MTAP inhibitor, thereby increasing levels of MTA in the lungs of the subject. The term "endogenous MTA" refers to MTA in the subject and excludes MTA that has been administered to the subject.

A further aspect the invention relates to a method of inhibiting polyamine synthesis in the lungs of a subject, comprising administering to the subject an effective amount of a transition state MTAP inhibitor, thereby inhibiting polyamine synthesis in the lungs of the subject.

In some embodiments, the subject is one that has a lung disease, e.g., any lung disease in which airway inflammation is a cause and/or symptom, including, without limitation, CF, COPD, asthma, acute or chronic bronchitis, primary ciliary dyskinesia, bronchiectasis (e.g., idiopathic bronchiectasis), acute respiratory distress syndrome, or any combination thereof.

An additional aspect the invention relates to a method of inhibiting inflammation in the lungs of a subject, comprising administering to the subject an effective amount of a transition state MTAP inhibitor, thereby inhibiting lung inflammation in the subject. The subject may be one that has or is suspected of having any lung disease in which airway inflammation is a cause and/or symptom, e.g., CF or COPD.

In some embodiments, the MTAP inhibitor is administered after the onset of inflammation, e.g., after signs of inflammation or related symptoms have been detected in the subject. In other embodiments, the MTAP inhibitor is administered prior to the onset of inflammation, e.g., prophylactically, e.g., to a subject that is known to have or is suspected of having a lung disease associated with inflammation but before signs of inflammation or related symptoms have been detected in the subject. Such prophylactic treatment is intended to delay the onset of inflammation and/or lessen the severity of inflammation in the subject. In certain embodiments, the MTAP inhibitor is administered both prior to and after the onset of inflammation.

Another aspect the invention relates to a method of treating a lung disease associated with inflammation in a subject in need thereof, comprising administering to the subject a therapeutically effective amount of a transition state MTAP inhibitor, thereby treating the lung disease associated with inflammation in the subject. A lung disease associated with inflammation is any lung disease in which inflammation of the airways is a cause and/or symptom. In some embodiments, the lung disease is an acute or chronic inflammatory lung disease including, without limitation, CF, COPD, asthma, acute or chronic bronchitis, or any combination thereof.

In any of the methods of the invention, the MTAP inhibitor may be administered chronically, e.g., prophylactically, e.g., continuously regardless of the appearance of symptoms of inflammation. In other embodiments, the MTAP inhibitor may be administered on an as needed basis, e.g., therapeutically, e.g., at a time of pulmonary exacerbation of symptoms.

In certain embodiments, the methods of the invention further comprise administering to the subject a second agent, e.g., a therapeutic agent. The additional agents can be delivered concurrently with the compounds of the invention. As used herein, the word "concurrently" means sufficiently close in time to produce a combined effect (that is, concurrently can be simultaneously, or it can be two or more events occurring within a short time period before or after each other).

The second agent may be an agent that treats and/or prevents one or more causes or symptoms of an inflammatory lung disease. The second agent may be, without limitation, a bronchodilator, hypertonic saline solution, dornase alpha, an antibiotic, an anti-inflammatory agent (e.g., a broad-based anti-inflammatory modulator such as ibuprofen or corticosteroids), an antibacterial with anti-inflammatory properties (e.g., azithromycin, anti-PcrV antibody (KB-001A)), a modulator of intracellular signaling (e.g., interferon-γ (actimmune), L-arginine, simvastatin, thiazolidinediones), an inhibitor of neutrophil influx (e.g., anti-IL-17, LTB4 RA (BIIL 284 BS)), a CXCR2 antagonist (e.g., SB-656933), an anti-oxidant (e.g., N-acetyl cysteine, β-carotene, glutathione, omega-3 fatty acids, vitamin C, vitamin E), an anti-protease (e.g., α1-protease inhibitor (plasma derived and transgenic), DMP-777, EPI-hNE4 (Depalstat), a monocyte/neutrophil elastase inhibitor, a recombinant secretory leukoprotease inhibitor), lumacaftor, ivacaftor, a disulfide reducing agent, or any combination thereof.

In one embodiment, the MTAP inhibitor and optionally the second agent are administered directly to a subject. Generally, the compounds of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. They can be delivered directly to the site of the disease or disorder, such as lungs. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100.0 mg/kg. Wide variations in the needed dosage are to be expected in view of the variety of compounds available and the differing efficiencies of various routes of administration. For example, oral administration (e.g., up to about 10-100 mg/kg) would be expected to require higher dosages than administration by intravenous or subcutaneous administration (e.g., up to about 0.1-10 mg/kg).

Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the compounds in a suitable delivery vehicle (e.g., polymeric microparticles or implantable devices) may increase the efficiency of delivery, particularly for oral delivery.

In some embodiments of the methods of the invention, the subject is a human. In other embodiments, the subject is an animal model of disease, e.g., a lung disease such as CF or COPD.

In one embodiment, the MTAP inhibitor is methylthio-DADMe-Immucillin-A (MTDIA).

The MTAP inhibitor may be one or more of the embodiments listed below.

1. A compound of formula (I):

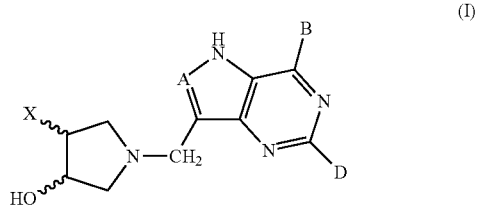

wherein
X is alkyl, cycloalkyl alkenyl, alkynyl, or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or $NR^2R^3$, wherein each alkylthio, arylthio and aralkylthio is optionally substituted with one or more alkyl, halogen, amino, hydroxy, or alkoxy; or
X is $SR^1$; or
X is $NR^2R^3$;

$R^1$, $R^2$ and $R^3$ are independently selected from alkyl, alkenyl, alkynyl, aralkyl, or aryl, each of which is optionally substituted with one or more substituents selected from hydroxy, alkoxy, thiol, alkylthio, arylthio, aralkylthio, halogen, carboxylic acid, carboxylate alkyl ester, nitro, cyano or $NR^2R^3$, wherein each alkylthio, arylthio, and aralkylthio is optionally substituted with one or more alkyl, halogen, amino, hydroxy, or alkoxy;
A is N or CH;
B is $NH_2$ or $NHR^4$;
$R^4$ is alkyl, alkenyl, alkynyl, aralkyl, aralkenyl, aralkynyl, or aryl, each of which is optionally substituted with one or more halogen or hydroxyl; and
D is H, OH, $NH_2$, or $SCH_3$;
or a tautomer thereof, or a pharmaceutically acceptable salt thereof, or an ester prodrug form thereof;
provided that when B is $NH_2$, D is H and A is CH, X is not propyl, phenylethyl, $CH_2SQ$, $CH_2OH$, or $CH_2OQ$, wherein Q is optionally substituted alkyl, aralkyl, or aryl.

2. A compound of formula (Ia):

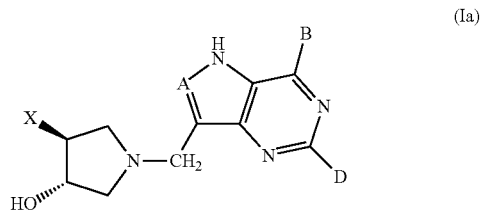

wherein
X, A, B and D are as defined above;
provided that when B is $NH_2$, D is H and A is CH, X is not propyl, phenylethyl, $CH_2SQ$, $CH_2OH$, or $CH_2OQ$, wherein Q is optionally substituted alkyl, aralkyl, or aryl;
or a tautomer thereof, or a pharmaceutically acceptable salt thereof, or an ester prodrug form thereof.

3. A compound of formula (Ib):

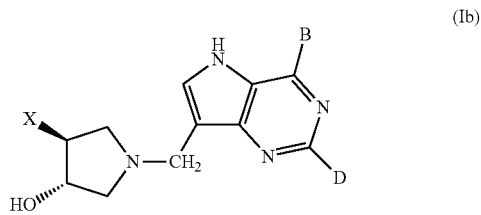

where X is as defined in 2 above provided that X is not propyl, phenylethyl, CH2SQ, CH2OH or CH2OQ, where Q is an optionally substituted alkyl, aralkyl or aryl group, or a tautomer thereof, or a pharmaceutically acceptable salt thereof, or an ester prodrug form thereof.

4. A compound as described in embodiments 1 to 3 wherein X is alkenyl or alkynyl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or $NR^2R^3$, wherein each alkylthio, arylthio, and aralkylthio group is optionally substituted with one or more alkyl, halogen, amino, hydroxy, or alkoxy.

5. A compound as described in embodiments 1 to 3 wherein X is alkyl which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, wherein each alkylthio, arylthio, and aralkylthio is optionally substituted with one or more alkyl, halogen, amino, hydroxy, or alkoxy.

6. A compound as described in embodiments 1 to 3 wherein X is cycloalkyl which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, where each alkylthio, arylthio, and aralkylthio group is optionally substituted with one or more alkyl, halogen, amino, hydroxy, or alkoxy.

7. A compound described in embodiments 1 to 3 wherein X is cycloalkyl wherein one or more of the ring atoms is a heteroatom.

8. A compound as described in embodiments 1 to 3 wherein X is aryl which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, wherein each alkylthio, arylthio, and aralkylthio group is optionally substituted with one or more alkyl, halogen, amino, hydroxy, or alkoxy.

9. A compound as described in embodiments 1 to 3 wherein X is SR$^1$, wherein R$^1$ is alkyl, alkenyl, alkynyl, aralkyl or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, wherein each alkylthio, arylthio, and aralkylthio group is optionally substituted with one or more alkyl, halogen, amino, hydroxy, or alkoxy.

10. A compound as described in embodiments 1 to 3 wherein X is NR$^2$R$^3$, wherein R$^2$ and R$^3$ are independently selected from alkyl, alkenyl, alkynyl, aralkyl or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, wherein each alkylthio, arylthio, and aralkylthio group is optionally substituted with one or more alkyl, halogen, amino, hydroxy, or alkoxy.

11. A compound as described in embodiments 1, 2, or 4 to 10 wherein B is NH$_2$.

12. A compound as described in embodiments 1, 2, or 4 to 11 wherein A is CH.

13. A compound selected from the group consisting of:
(3R,4S)-1-[(9-deazaadenin-9-yl)methyl]-3-hydroxy-4-(methylthiomethyl)pyrrolidine, or (methylthio-DADMe-Immucillin-A: MTDIA);
(3R,4S)-1-[(9-deazaadenin-9-yl)methyl]-3-hydroxy-4-(ethylthiomethyl)pyrrolidine;
(3R,4S)-1-[(9-deazaadenin-9-yl)methyl]-4-ethyl-3-hydroxy-pyrrolidine;
(3R,4S)-1-[(9-deazaadenin-9-yl)methyl]-3-hydroxy-4-(n-propylthiomethyl)pyrrolidine;
(3R,4S)-1-[(9-deazaadenin-9-yl)methyl]-3-hydroxy-4-propylpyrrolidine;
(3R,4S)-1-[(9-deazaadenin-9-yl)methyl]-3-hydroxy-4-(isopropylthiomethyl)pyrrolidine;
(3R,4S)-1-[(9-deazaadenin-9-yl)methyl]-3-hydroxy-4-isopropylpyrrolidine;
(3R,4S)-1-[(9-deazaadenin-9-yl)methyl]-3-hydroxy-4-(n-butylthiomethyl)pyrrolidine;
(3R,4S)-1-[(9-deazaadenin-9-yl)methyl]-4-butyl-3-hydroxy-pyrrolidine;
(3R,4S)-1-[(9-deazaadenin-9-yl)methyl]-3-hydroxy-4-(phenylthiomethyl)pyrrolidine;
(3R,4S)-1-[(9-deazaadenin-9-yl)methyl]-4-benzyl-3-hydroxy-pyrrolidine;
(3R,4S)-1-[(9-deazaadenin-9-yl)methyl]-3-hydroxy-4-(4-chlorophenylthiomethyl)pyrrolidine;
(3R,4S)-1-[(9-deazaadenin-9-yl)methyl]-3-hydroxy-4-(4-chlorophenylmethyl)pyrrolidine;
(3R,4S)-1-[(9-deazaadenin-9-yl)methyl]-3-hydroxy-4-(3-chlorophenylthiomethyl)pyrrolidine;
(3R,4S)-1-[(9-deazaadenin-9-yl)methyl]-3-hydroxy-4-(3-chlorophenylmethyl)pyrrolidine;
(3R,4S)-1-[(9-deazaadenin-9-yl)methyl]-3-hydroxy-4-(benzylthiomethyl)pyrrolidine;
(3R,4S)-1-[(9-deazaadenin-9-yl)methyl]-3-hydroxy-4-(4-fluorophenylthiomethyl)pyrrolidine;
(3R,4S)-1-[(9-deazaadenin-9-yl)methyl]-3-hydroxy-4-(4-fluorophenylmethyl)pyrrolidine;
(3R,4S)-1-[(9-deazaadenin-9-yl)methyl]-3-hydroxy-4-(4-pyridylthiomethyl)pyrrolidine;
(3R,4S)-1-[(9-deazaadenin-9-yl)methyl]-3-hydroxy-4-(4-pyridylmethyl)pyrrolidine;
(3R,4S)-1-[(9-deazaadenin-9-yl)methyl]-3-hydroxy-4-(ethylphenylthiomethyl)pyrrolidine;
(3R,4S)-1-[(9-deazaadenin-9-yl)methyl]-3-hydroxy-4-phenylethylpyrrolidine;
(3R,4R)-1-[(9-deazaadenin-9-yl)methyl]-3-acetoxy-4-(acetoxymethyl)pyrrolidine;
(3R,4S)-1-[(9-deazaadenin-9-yl)methyl]-3-hydroxy-4-(cyclohexylthiomethyl)pyrrolidine;
(3R,4S)-1-[(9-deazaadenin-9-yl)methyl]-3-hydroxy-4-(cyclohexylmethyl)pyrrolidine;
(3R,4S)-1-[(9-deazaadenin-9-yl)methyl]-3-hydroxy-4-(homocysteinylmethyl)pyrrolidine; (3R,4S)-1-[(9-deazaadeniri-9-yl)methyl]-3-hydroxy-4-(benzyloxymethyl)pyrrolidine;
(3R,4S)-1-[(9-deazaadenin-9-yl)methyl]-3-hydroxy-4-(methoxymethyl)pyrrolidine;
(3R,4S)-1-[(9-deazaadenin-9-yl)methyl]-3-hydroxy-4-(cyclohexylmethylthiomethyl)pyrrolidine;
(3R,4S)-1-[(9-deazaadenin-9-yl)methyl]-3-hydroxy-4-(cycloheptylthiomethyl)pyrrolidine;
(3R,4S)-1-[(9-deazaadenin-9-yl)methyl]-3-hydroxy-4-(cycloheptylmethyl)pyrrolidine;
(3R,4S)-1-[(9-deazaadenin-9-yl)methyl]-3-hydroxy-4-(cycloheptylmethylthiomethyl)pyrrolidine; (3R,4S)-1-[(9-deazaadenin-9-yl)methyl]-3-hydroxy-4-(cyclopentylthiomethyl)pyrrolidine;
(3R,4S)-1-[(9-deazaadenin-9-yl)methyl]-3-hydroxy-4-(cyclopentylmethylthiomethyl)pyrrolidine; (3R,4S)-1-[(9-deazaadenin-9-yl)methyl]-3-hydroxy-4-(cyclopentylmethyl)pyrrolidine;
(3R,4S)-1-[(9-deazaadenin-9-yl)methyl]-3-hydroxy-4-(cyclobutylthiomethyl)pyrrolidine;
(3R,4S)-1-[(9-deazaadenin-9-yl)methyl]-3-hydroxy-4-(cyclobutylmethyl)pyrrolidine;
(3R,4S)-1-[(9-deazaadenin-9-yl)methyl]-3-hydroxy-4-(cyclopropylthiomethyl)pyrrolidine;
(3R,4S)-1-[(9-deazaadenin-9-yl)methyl]-3-hydroxy-4-(cyclopropylmethyl)pyrrolidine;
(±)-trans-1-[(9-deaza-adenin-9-yl)methyl]-3-hydroxy-4-phenylpyrrolidine;
(±)-trans-1-[(9-deaza-adenin-9-yl)methyl]-3-hydroxy-4-vinylpyrrolidine;
(±)-trans-1-[(9-deaza-adenin-9-yl)methyl]-3-hydroxypyrrolidine;

(±)-trans-4-allyl-1-[(9-deaza-adenin-9-yl)methyl]-3-hydroxypyrrolidine;
(±)-trans-4-cyclopropyl-1-[(9-deaza-adenin-9-yl)methyl]-3-hydroxypyrrolidine;
(±)-trans-4-cyclohexyl-1-[(9-deaza-adenin-9-yl)methyl]-3-hydroxypyrrolidine;
(±)-trans-4-cyclohexylmethyl-1-[(9-deaza-adenin-9-yl)methyl]-3-hydroxypyrrolidine;
(±)-trans-1-[(9-deaza-adenin-9-yl)methyl]-3-hydroxy-4-prop-1-en-2-yl-pyrrolidine;
(±)-trans-1-[(9-deaza-adenin-9-yl)methyl]-4-ethyl-3-hydroxypyrrolidine;
(±)-trans-4-butyl-1-[(9-deaza-adenin-9-yl)methyl]-3-hydroxypyrrolidine;
(±)-trans-1-[(9-deaza-adenin-9-yl)methyl]-3-hydroxy-4-pent-3-yl-pyrrolidine;
(±)-trans-4-cyclopentyl-1-[(9-deaza-adenin-9-yl)methyl]-3-hydroxypyrrolidine;
(±)-trans-1-[(9-deaza-adenin-9-yl)methyl]-3-hydroxy-4-(1H-1,2,3-triazol-1-yl)pyrrolidine;
(±)-trans-4-(1-benzyl-1H-1,2,3-triazol-4-yl)-1-[(9-deaza-adenin-9-yl)methyl]-3-hydroxypyrrolidine;
(±)-trans-4-(3-benzylthiopropyl)-1-[(9-deaza-adenin-9-yl)methyl]-3-hydroxypyrrolidine;
(3R,4S)-4-butyl-1-[(9-deaza-adenin-9-yl)methyl]-3-hydroxypyrrolidine;
(±)-c/s-1-[(9-deaza-adenin-9-yl)methyl]-4-ethyl-3-hydroxypyrrolidine;
(3R,4S)-1-[(9-deaza-adenin-9-yl)methyl]-3-hydroxy-4-phenylpyrrolidine;
(3R,4S)-1-[(9-deaza-adenin-9-yl)methyl]-3-hydroxy-4-vinylpyrrolidine;
(3R,4S)-1-[(9-deaza-adenin-9-yl)methyl]-4-ethenyl-3-hydroxy-pyrrolidine;
(3R,4S)-4-allyl-1-[(9-deaza-adenin-9-yl)methyl]-3-hydroxypyrrolidine;
(3R,4S)-4-cyclopropyl-1-[(9-deaza-adenin-9-yl)methyl]-3-hydroxypyrrolidine;
(3R,4S)-4-cyclohexyl-1-[(9-deaza-adenin-9-yl)methyl]-3-hydroxypyrrolidine;
(3R,4S)-4-cyclohexylmethyl-1-[(9-deaza-adenin-9-yl)methyl]-3-hydroxypyrrolidine;
(3R,4S)-1-[(9-deaza-adenin-9-yl)methyl]-3-hydroxy-4-prop-1-en-2-yl-pyrrolidine;
(3R,4S)-4-butyl-1-[(9-deaza-adenin-9-yl)methyl]-3-hydroxypyrrolidine;
(3R,4S)-1-[(9-deaza-adenin-9-yl)methyl]-3-hydroxy-4-pent-3-yl-pyrrolidine;
(3R,4S)-4-cyclopentyl-1-[(9-deaza-adenin-9-yl)methyl]-3-hydroxypyrrolidine
(3 S,4S)-1-[(9-deaza-adenin-9-yl)methyl]-3-hydroxy-4-(1H-1,2,3-triazol-1-yl)pyrrolidine;
(3R,4R)-4-(1-benzyl-1H-1,2,3-triazol-4-yl)-1-[(9-deaza-adenin-9-yl)methyl]-3-hydroxypyrrolidine;
(3R,4S)-4-(3-benzylthiopropyl)-1-[(9-deaza-adenin-9-yl)methyl]-3-hydroxypyrrolidine;
(3 S,4R)-1-[(9-deaza-adenin-9-yl)methyl]-4-ethyl-3-hydroxypyrrolidine;
(±)-trans-1-[(9-deaza-adenin-9-yl)methyl]-3-hydroxy-4-(2-methylpropyl)pyrrolidine;
(3R,4S)-1-[(9-deaza-adenin-9-yl)methyl]-3-hydroxy-4-(2-methylpropyl)pyrrolidine;
(±)-trans-4-butyl-1-[(9-deaza-adenin-9-yl)methyl]-3-hydroxypyrrolidine;
(3R,4S)-4-butyl-1-[(9-deaza-adenin-9-yl)methyl]-3-hydroxypyrrolidine;
(±)-trans-1-[(9-deaza-adenin-9-yl)methyl]-3-hydroxy-4-(thiazol-2-yl)-pyrrolidine;
(3R,4S)-1-[(9-deaza-adenin-9-yl)methyl]-3-hydroxy-4-(thiazol-2-yl)-pyrrolidine;
(±)-trans-1-[(9-deaza-adenin-9-yl)methyl]-3-hydroxy-4-(tetrazol-5-yl)-pyrrolidine;
(3R,4R)-1-[(9-deaza-adenin-9-yl)methyl]-3-hydroxy-4-(tetrazol-5-yl)-pyrrolidine;
or a tautomer thereof, or a pharmaceutically acceptable salt thereof, or an ester prodrug form thereof.

14. A compound of formula (II):

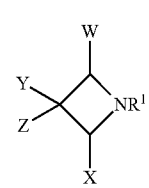

(II)

wherein
W and X are each independently selected from hydrogen, $CH_2OH$, $CH_2OQ$ and $CH_2SQ$;
Y and Z are each independently selected from hydrogen, halogen, $CH_2OH$, $CH_2OQ$, $CH_2SQ$, SQ, OQ and Q;
Q is alkyl, aralkyl, or aryl, each of which may be optionally substituted with one or more substituents selected from hydroxy, halogen, methoxy, amino, or carboxy;
$R^1$ is a radical of formula (III):

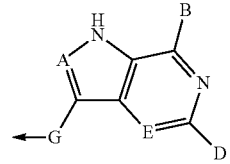

(III)

or
$R^1$ is a radical of formula (IV):

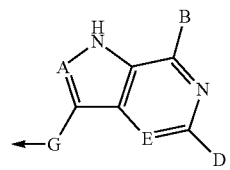

(IV)

A is selected from N, CH and $CR^2$;
$R^2$ is selected from halogen, alkyl, aralkyl, aryl, OH, $NH_2$, $NHR^3$, $NR^3R^4$ or $SR^5$;
$R^3$, $R^4$, and $R^5$ are each independently alkyl, aralkyl, or aryl optionally substituted with hydroxyl or halogen, and wherein $R^2$ is optionally substituted with hydroxy or halogen when $R^2$ is alkyl, aralkyl or aryl;
B is selected from hydroxy, $NH_2$, $NHR^6$, SH, hydrogen, or halogen;
$R^6$ is alkyl, aralkyl, or aryl optionally substituted with hydroxy or halogen;
D is selected from hydroxy, $NH_2$, $NHR^7$, hydrogen, halogen, or $SCH_3$;

$R^7$ is alkyl, aralkyl, or aryl group optionally substituted with hydroxy or halogen;

E is selected from N and CH;

G is $C_{1-4}$ saturated or unsaturated alkyl optionally substituted with hydroxy or halogen, or G is absent;

or a tautomer thereof, or a pharmaceutically acceptable salt thereof, or an ester thereof, or a prodrug thereof.

15. A compound as described in embodiment 14 wherein W is $CH_2OH$ or $CH_2SQ$.

16. A compound as described in embodiment 15 wherein W is $CH_2SCH_3$.

17. A compound as described in embodiment 14 wherein X is $CH_2OH$ or $CH_2SQ$.

18. A compound as described in embodiment 15 wherein W is $CH_2SCH_3$.

19. A compound as described in any one of embodiments 14 to 18 wherein Z is selected from hydrogen, halogen, $CH_2OH$, $CH_2OQ$, or $CH_2SQ$.

20. A compound as described in embodiment 19 wherein Y or Z is $CH_2OH$.

21. A compound as described in embodiment 19 wherein Y or Z is $CH_2SQ$ or $CH_2OQ$.

22. A compound as described in embodiment 19 wherein either or both of Y or Z is Q.

23. A compound as described in embodiment 19 where either or both of Y or Z is $CH_2OH$.

24. A compound as described in embodiment 14 wherein W and X are both hydrogen.

25. A compound as described in embodiment 24 wherein either or both of Y or Z is $CH_2OH$.

26. A compound as described in embodiment 24 wherein either or both of Y or Z is $CH_2SQ$.

27. A compound as described in embodiment 14 wherein Y and Z are both hydrogen.

28. A compound as described in embodiment 27 wherein either or both of Y or Z is $CH_2OH$.

29. A compound as described in any one of embodiments 14 to 28 wherein G is $CH_2$.

30. A compound as described in any of embodiments 14 to 29 wherein $R^1$ is a radical of formula (III).

31. A compound as described in any one of embodiments 14 to 29 wherein $R^1$ is a radical of formula (IV).

32. A compound as described in any one of embodiments 14 to 31 wherein B is hydroxyl or $NH_2$.

33. A compound as described in any one of embodiments 14 to 32 wherein A is CH or N.

34. A compound as described in any one of embodiments 14 to 33 wherein D is H or $NH_2$.

35. A compound as described in any one of embodiments 14 to 34 wherein E is N.

36. A compound as described in any one of embodiments 14 to 35 wherein, when any of Y, Z, B and D is halogen, each halogen is independently chlorine or fluorine.

37. A compound of formula (V):

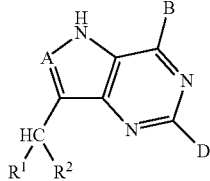

(V)

wherein $R^1$ is H or $NR^3R^4$;

$R^2$ is H or alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio group is optionally substituted with one or more alkyl, halogen, amino, hydroxy, or alkoxy;

provided that when $R^1$ is H, $R^2$ is alkyl, alkenyl, alkynyl, aralkyl, aralkenyl, aralkynyl, or aryl which is substituted with at least one $NR^3R^4$;

$R^3$ and $R^4$, independently of each other, are H or is alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio and aralkylthio group is optionally substituted with one or more alkyl, halogen, amino, hydroxy, or alkoxy;

A is N or CH;

B is OH or alkoxy; and

D is H, OH, $NH_2$, or $SCH_3$;

provided that when $R^1$ is $NR^3R^4$, $R^2$ is H, A is CH, B is OH, and D is H, then $R^3$ is not hydroxyethyl or hydroxypropyl when $R^4$ is hydroxyethyl; and provided that when $R^1$ is $NR^3R^4$, $R^2$ is H, A is CH, B is OH, and D is $NH_2$, then $R^3$ is not hydroxyethyl when $R^4$ is H, methyl, ethyl, or hydroxyethyl, and $R^4$ is not hydroxyethyl when $R^3$ is H, methyl, ethyl, or hydroxyethyl;

or a tautomer thereof, or a pharmaceutically acceptable salt thereof, or an ester prodrug form thereof.

38. A compound as described in embodiment 37 wherein $R^1$ is H and $R^2$ is alkyl substituted with at least one $NR^3R^4$ group.

39. A compound as described in embodiments 37 or 38 wherein $R^3$ and $R^4$, independently of each other, are optionally substituted alkyl or H.

40. A compound as described in embodiment 39 wherein $R^3$ or $R^4$ is optionally substituted $C_1$-$C_5$ alkyl.

41. A compound as described in embodiment 39 wherein $R^3$ or $R^4$ is $C_1$-$C_5$ alkyl optionally substituted by one or more hydroxy.

42. A compound as described in embodiment 41 wherein $R^3$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

43. A compound as described in embodiment 40 wherein $R^3$ or $R^4$ is $C_1$-$C_5$ alkyl substituted by one or more hydroxy and/or one or more optionally substituted thiol, alkylthio, arylthio, or aralkylthio.

44. A compound as described in embodiment 43 wherein $R^3$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

45. A compound as described in embodiment 37 wherein $R^1$ is $NR^3R^4$, $R^3$ and $R^4$ are H, and $R^2$ is alkyl optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio is optionally substituted with one or more alkyl, halogen, amino, hydroxy, or alkoxy.

46. A compound as described in embodiment 45 wherein $R^2$ is optionally substituted $C_1$-$C_5$ alkyl.

47. A compound as described in embodiment 46 wherein $R^2$ is $C_1$-$C_5$ alkyl optionally substituted by one or more hydroxy groups.

48. A compound as described in embodiment 47 wherein $R^2$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

49. A compound as described in embodiment 48 wherein $R^2$ is $C_1$-$C_5$ alkyl substituted by one or more hydroxy and/or one or more optionally substituted thiol, alkylthio, arylthio, or aralkylthio.

50. A compound as described in embodiment 49 wherein $R^2$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

51. A compound as described in embodiment 37 wherein $R^1$ is $NR^3R^4$, $R^3$ is H, $R^4$ is alkyl optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio is optionally substituted with one or more alkyl, halogen, amino, hydroxy, or alkoxy, and $R^2$ is H.

52. A compound as described in embodiment 51 wherein $R^4$ is optionally substituted $C_1$-$C_5$ alkyl.

53. A compound as described in embodiment 52 wherein $R^4$ is $C_1$-$C_5$ alkyl optionally substituted by one or more hydroxy.

54. A compound as described in embodiment 53 wherein $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

55. A compound as described in embodiment 54 wherein $R^4$ is $C_1$-$C_5$ alkyl substituted by one or more hydroxy and/or one or more optionally substituted thiol, alkylthio, arylthio, or aralkylthio.

56. A compound as described in embodiment 55 wherein $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or rnethylthiotetrahydroxypentyl.

57. A compound as described in embodiment 37 wherein $R^1$ is $NR^3R^4$, $R^3$ is H, $R^4$ and $R^2$ are alkyl optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio group is optionally substituted with one or more alkyl, halogen, amino, hydroxy, or alkoxy.

58. A compound as described in embodiment 57 wherein $R^2$ or $R^4$ is optionally substituted $C_1$-$C_5$ alkyl.

59. A compound as described in embodiment 58 wherein $R^2$ or $R^4$ is $C_1$-$C_5$ alkyl optionally substituted by one or more hydroxy.

60. A compound as described in embodiment 58 wherein $R^2$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

61. A compound as described in embodiment 59 wherein $R^2$ or $R^4$ is $C_1$-$C_5$ alkyl substituted by one or more hydroxy and/or one or more optionally substituted thiol, alkylthio, arylthio, or aralkylthio.

62. A compound as described in embodiment 61 wherein $R^2$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

63. A compound as described in embodiment 37 wherein $R^1$ is $NR^3R^4$, $R^3$ and $R^4$ are each alkyl optionally substituted with one or more hydroxy, alkoxy, thiol, alkylthio, arylthio, aralkylthio, halogen, carboxylic acid, carboxylate alkyl, ester, nitro, or $NR^3R^4$, where each alkylthio, arylthio, and aralkylthio is optionally substituted with one or more alkyl, halogen, amino, hydroxy, or alkoxy, and $R^2$ is H.

64. A compound as described in embodiment 63 wherein $R^3$ or $R^4$ is optionally substituted $C_1$-$C_5$ alkyl.

65. A compound as described in embodiment 64 wherein $R^3$ or $R^4$ is $C_1$-$C_5$ alkyl optionally substituted by one or more hydroxy groups.

66. A compound as described in embodiment 65 wherein $R^3$ or $R^4$ is hydroxymethyl, hydroxyethyl, hydroxypropyl, dihydroxypropyl, hydroxybutyl, dihydroxybutyl, trihydroxybutyl, hydroxypentyl, dihydroxypentyl, or trihydroxypentyl.

67. A compound as described in embodiment 65 wherein $R^3$ or $R^4$ is $C_1$-$C_5$ alkyl substituted by one or more hydroxy and/or one or more optionally substituted thiol, alkylthio, arylthio, or aralkylthio.

68. A compound as described in embodiment 67 wherein $R^3$ or $R^4$ is methylthiomethyl, methylthioethyl, methylthiopropyl, methylthiohydroxypropyl, methylthiodihydroxypropyl, methylthiobutyl, methylthiohydroxybutyl, methylthiodihydroxybutyl, methylthiotrihydroxybutyl, methylthiopentyl, methylthiohydroxypentyl, methylthiodihydroxypentyl, methylthiotrihydroxypentyl, or methylthiotetrahydroxypentyl.

69. A compound as described in any one of embodiments 37 to 68 wherein A is CH.

70. A compound as described in any one of embodiments 37 to 68 wherein A is N.

71. A compound as described in any one of embodiments 37 to 70 wherein B is OH.

72. A compound as described in any one of embodiments 37 to 71 wherein D is H or $NH_2$.

73. A compound as claimed in any one of claims embodiments 36 to 70 wherein D is OH or $SCH_3$.

74. A compound as described in embodiment 37 which is:
rac-(2R,3 S)-3-((4-hydroxy-5H-pyrrolo[3,2-d]pyrimidin-7-yl)methylamino)butane-1,2,4-triol;
7-(((2,4-dihydroxybutyl)(methyl)amino)methyl)-3H-pyrrolo[3,2-d]pyrimidin-4(5H)-one;
(2R,3 S)-3-((4-hydroxy-5H-pyrrolo[3,2-d]pyrimidin-7-yl)methylamino)-propane-1,2-diol hydrochloride;
(2R,3 S)-3-((4-hydroxy-5H-pyrrolo[3,2-d]pyrimidin-7-yl)methylamino)butane-1,2,4-triol hydrochloride;
2-amino-7-(2,3-dihydroxy-1-(2-hydroxyethylamino)propyl)-3H-pyrrolo[3,2-d]pyrimidin-4(5H)-one;
7-(2,3-dihydroxy-1-(2-hydroxyethylamino)propyl)-3H-pyrrolo[3,2-d]pyrimidin-4(5H)-one;
2-amino-7-(1-amino-2,3,5-trihydroxypentyl)-3H-pyrrolo[3,2-d]pyrimidin-4(5H)-one;

7-(1-amino-2,3,5-trihydroxypentyl)-3H-pyrrolo[3,2-d]pyrimidin-4(5H)-one;
2-amino-7-(4-amino-2,3,5-trihydroxypentyl)-3H-pyrrolo[3,2-d]pyrimidin-4(5H)-one;
7-(4-amino-2,3,5-trihydroxypentyl)-3H-pyrrolo[3,2-d]pyrimidin-4(5H)-one;
2-amino-7-(1-(1,3-dihydroxypropan-2-ylamino)-2-hydroxyethyl)-3H-pyrrolo[3,2-d]pyrimidin-4(5H)-one;
7-(1-(1,3-dihydroxypropan-2-ylamino)-2-hydroxyethyl)-3H-pyrrolo[3,2-d]pyrimidin-4(5H)-one;
2-amino-7-(((2,4-dihydroxybutyl)(methyl)amino)methyl)-3H-pyrrolo[3,2-d]pyrimidin-4(5H)-one;
2-amino-7-((2,4-dihydroxybutylamino)methyl)-3H-pyrrolo[3,2-d]pyrimidin-4(5H)-one;
7-((2,4-dihydroxybutylamino)methyl)-3H-pyrrolo[3,2-d]pyrimidin-4(5H)-one;
2-amino-7-((3,4-dihydroxy-2-(hydroxymethyl)butylamino)methyl)-3H-pyrrolo[3,2-d]pyrimidin-4(5H)-one;
7-((3)4-dihydroxy-2-(hydroxymethyl)butylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
7-((3-hydroxy-2-(hydroxymethyl)propylamino)methyl)-3H-pyrrolo[3,2-d]pyrimidin-4(5H)-one;
2-amino-7-(((3-hydroxy-2-(hydroxymethyl)propyl)(methyl)amino)methyl)-3H-pyrrolo[3,2-d]pyrimidin 4(5H)-one;
7-(((3-hydroxy-2-(hydroxymethyl)propyl)(methyl)amino)methyl)-3H-pyrrolo[3,2-d]pyrimidin-4(5H)-one;
2-amino-7-(3,4-dihydroxy-5-(methylthiomethyl)pyrrolidin-2-yl)-3H-pyrrolo[3,2-d]pyrimidin-4(5H)-one;
7-(3,4-dihydroxy-5-(methylthiomethyl)pyrrolidin-2-yl)-3H-pyrrolo[3,2-d]pyrimidin-4(5H)-one;
2-amino-7-(2,3-dihydroxy-1-(2-(methylthio)ethylamino)propyl)-3H-pyrrolo[3,2-d]pyrimidin-4(5H)-one;
7-(2,3-dihydroxy-1-(2-(methylthio)ethylamino)propyl)-3H-pyrrolo[3,2-d]pyrimidiyl-4(5H)-one;
2-amino-7-(1-amino-2,3-dihydroxy-5-(methylthio)pentyl)-3H-pyrrolo[3,2-d]pyrimidin-4(5H)-one;
7-(1-amino-2,3-dihydroxy-5-(methylthio)pentyl-5H-pyrrolo[3,2-d]pyrimidin-4(5H)-one;
2-amino-7-(2-hydroxy-1-(1-hydroxy-3-(methylthio)propan-2-ylamino)ethyl)-3H-pyrrolo[3,2-d]pyrimidin-4(5H)-one;
7-(2-hydroxy-1-(1-hydroxy-3-(methylthio)propan-2-ylamino)ethyl)-3H-pyrrolo[3,2-d]pyrimidin-4(5H)-one;
2-amino-7-((3,4-dihydroxy-1-(methylthio)butan-2-ylamino)methyl)-3H-pyrrolo[3,2-d]pyrimidin-4(5H)-one;
7-((3,4-dihydroxy-1-(methylthio)butan-2-ylamino)methyl)-3H-pyrrolo[3,2-d]pyrimidin-4(5H)-one;
2-amino-7-(((2-hydroxy-4-(methylthio)butyl)(methyl)amino)methyl)-3H-pyrrolo[3,2-d]pyrimidin-4(5H)-one;
7-(((2-hydroxy-4-(methylthio)butyl)(methyl)amino)methyl)-3H-pyrrolo[3,2-d]pyrimidin-4(5H)-one;
2-amino-7-((2-hydroxy-4-(methylthio)butylamino)methyl)-3H-pyrrolo[3,2-d]pyrimidin-4(5H)-one;
7-((2-hydroxy-4-(methylthio)butylamino)methyl)-3H-pyrrolo[3,2-d]pyrimidin-4(5H)-one;
2-amino-7-((3,4-dihydroxy-2-(methylthiomethyl)butylamino)methyl)-3H-pyrrolo[3,2-d]pyrimidin-4(5H)-one;
7-((3,4-dihydroxy-2-(methylthiomethyl)butylamino)methyl)-3H-pyrrolo[3,2-d]pyrimidin-4(5H)-one;
2-amino-7-((3-hydroxy-2-(methylthiomethyl)propylamino)methyl)-3H-pyrrolo[3,2-d]pyrimidin-4(5H)-one;
7-((3-hydroxy-2-(methylthiomethyl)propylamino)methyl)-3H-pyrrolo[3,2-d]pyrimidin-4(5H)-one;
7-(((3-hydroxy-2-(methylthiomethyl)propyl)(methyl)amino)methyl)-3H-pyrrolo[3,2-d]pyrimidin-4(5H)-one;
2-amino-7-(((3-hydroxy-2-(methylthiomethyl)propyl)(methyl)amino)methyl)-3H-pyrrolo[3,2-d]pyrimidin-4(5H)-one;
7-(((2R,3R)-1,3,4-trihydroxybutan-2-ylamino)methyl)-3H-pyrrolo[3,2-d]pyrimidin-4(5H)-one;
7-(((2S,3S)-1,3,4-trihydroxybutan-2-ylamino)methyl)-3H-pyrrolo[3,2-d]pyrimidin-4(5H)-one;
7-(((2R,3 S)-1,3,4-trihydroxybutan-2-ylamino)methyl)-3H-pyrrolo[3,2-d]pyrimidin-4(5H)-one;
7-(((2S,3 S)-1,3,4-trihydroxybutan-2-ylamino)methyl)-3H-pyrrolo[3,2-d]pyrimidin-4(5H)-one;
2-amino-7-(((2R,3R)-1,3,4-trihydroxybutan-2-ylamino)methyl)-3H-pyrrolo[3,2-d]pyrimidin-4(5H)-one;
2-amino-7-(((2S,3S)-1,3,4-trihydroxybutan-2-ylamino)methyl)-3H-pyrrolo[3,2-d]pyrimidin-4(5H)-one;
2-amino-7-(((2R,3 S)-1,3,4-trihydroxybutan-2-ylamino)methyl)-3H-pyrrolo[3,2-d]pyrimidin-4(5H)-one;
2-amino-7-(((2S,3R)-1,3,4-trihydroxybutan-2-ylamino)methyl)-3H-pyrrolo[3,2-d]pyrimidin-4(5H)-one;
5-amino-3-(((2R,3R)-1,3,4-trihydroxybutan-2-ylamino)methyl)-1H-pyrazolo[4,3-d]pyrimidin-7(6H)-one;
5-amino-3-(((2S,3S)-1,3,4-trihydroxybutan-2-ylamino)methyl)-1H-pyrazolo[4,3-d]pyrimidin-7(6H)-one;
5-amino-3-(((2R,3 S)-1,3,4-trihydroxybutan-2-ylamino)methyl)-1H-pyrazolo[4,3-d]pyrimidin-7(6H)-one;
5-amino-3-(((2S,3R)-1,3,4-trihydroxybutan-2-ylamino)methyl)-1H-pyrazolo[4,3-d]pyrimidin-7(6H)-one;
7-((1,3-dihydroxy-2-(hydroxymethyl)propan-2-ylamino)methyl)-3H-pyrrolo[3,2-d]pyrimidin-4(5H)-one;
2-amino-7-((1,3-dihydroxy-2-(hydroxymethyl)propan-2-ylamino)methyl)-3H-pyrrolo[3,2-d]pyrimidin-4(5H)-one;
3-((1,3-dihydroxy-2-(hydroxymethyl)propan-2-ylamino)methyl)-1H-pyrazolo[4,3-d]pyrimidin-7(6H)-one;
2-amino-7-((4-hydroxybutylamino)methyl)-3H-pyrrolo[3,2-d]pyrimidin-4(5H)-one;
3-((4-hydroxybutylamino)methyl)-1H-pyrazolo[4,3-d]pyrimidin-7(6H)-one;
7-((2-hydroxyethylamino)methyl)-3H-pyrrolo[3,2-d]pyrimidin-4(5H)-one;
2-amino-7-((2-hydroxyethylamino)methyl)-3H-pyrrolo[3,2-d]pyrimidin-4(5H)-one;
3-((2-hydroxyethylamino)methyl)-1H-pyrazolo[4,3-d]pyrimidin-7(6H)-one;
7-((3-hydroxy-2-(hydroxymethyl)propylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
3-(3-hydroxy-2-(hydroxymeth)propylamino)methyl)-1H-pyrazolo[3,2-d]-dipyrimidin-7(6H)-one;
7-(((3-hydroxy-2-(hydroxymethyl)propyl)(methyl)-amino)methyl)-3H-pyrrolo[3,2-d]pyrimidin-4(5H)-one;
2-amino-7-(((3-hydroxy-2-(hydroxymethyl)propyl)(methyl)-amino)methyl)-3H-pyrrolo[3,2-d]pyrimidin-4(5H)-one;
3-(((1,3-dihydroxypropan-2-yl)(methyl)amino)methyl)-1H-pyrazolo[4,3-d]pyrimidin-7(6H)-one;
7-((3-hydroxy-2-(hydroxymethyl)propylamino)methyl)-3H-pyrrolo[3,2-d]pyrimidin-4(5H)-one;
2-amino-7-((3-hydroxy-2-(hydroxymethyl)propylamino)methyl)-3H-pyrrolo[3,2-d]pyrimidin-4(5H)-one;
3-((1,3-dihydroxypropan-2-ylamino)methyl)-1H-pyrazolo[4,3-d]pyrimidin-7(6H)-one;
7-(((3-hydroxy-2-(hydroxymethyl)propyl)(methyl)-amino)methyl)-3H-pyrrolo[3,2-d]pyrimidin-4(5H)-one;

2-amino-7-(((3-hydroxy-2-(hydroxymethyl)propyl)
(methyl)-amino)methyl)-3H-pyrrolo[3,2-d]pyrimidin-4
(5H)-one;
3-(((1,3-dihydroxypropan-2-yl)(methyl)amino)methyl)-1H-
pyrazolo[4,3-d]pyrimidin-7(6H)-one;
7-(((3-hydroxy-2-(hydroxymethyl)propyl)(hydroxymethyl)
amino)methyl)-3H-pyrrolo[3,2-d]pyrimidin-4(5H)-one;
2-amino-7-(((3-hydroxy-2-(hydroxymethyl)propyl)(hy-
droxymethyl)amino)methyl)-3H-pyrrolo[3,2-d]pyrimi-
din-4(5H)-one;
5-amino-3-(((3-hydroxy-2-(hydroxymethyl)propyl)(hy-
droxymethyl)amino)methyl)-1H-pyrazolo[4,3d]pyrimi-
din-7(6H)-one;
7-((1,3-dihydroxy-2-(methylthiomethyl)propan-2-ylamino)
methyl)-3H-pyrrolo[3,2-d]pyrimidin-4(5H)-one;
2-amino-7-((1,3-dihydroxy-2-(methylthiomethyl)propan-2-
ylamino)methyl)-3H-pyrrolo[3,2-d]pyrimidin-4(5H)-
one;
5-amino-3-((1,3-dihydroxy-2-(methylthiomethyl)propan-2-
ylamino)methyl)-1H-pyrazolo[4,3-d]pyrimidin-7(6H)-
one;
7-(((2R,3R)-2,3,4-trihydroxybutylamino)methyl)-3H-pyr-
rolo[3,2-d]pyrimidin-4(5H)-one;
7-(((2S,3 S)-2,3,4-trihydroxybutylamino)methyl)-3H-pyr-
rolo[3,2-d]pyrimidin-4(5H)-one;
7-(((2R,3 S)-2,3,4-trihydroxybutylamino)methyl)-3H-pyr-
rolo[3,2-d]pyrimidin-4(5H)-one;
7-(((2S,3R)-2,3,4-trihydroxybutylamino)methyl)-3H-pyr-
rolo[3,2-d]pyrimidin-4(5H)-one;
2-amino-7-(((2R,3R)-2,3,4-trihydroxybutylamino)methyl)-
3H-pyrrolo[3,2-d]pyrimidin-4(5H)-one;
2-amino-7-(((2S,3 S)-2,3,4-trihydroxybutylamino)methyl)-
3H-pyrrolo[3,2-d]pyrimidin-4(5H)-one;
2-amino-7-(((2R,3 S)-2,3,4-trihydroxybutylamino)methyl)-
3H-pyrrolo[3,2-d]pyrimidin-4(5H)-one;
2-amino-7-(((2S,3R)-2,3,4-trihydroxybutylamino)methyl)-
3H-pyrrolo[3,2-d]pyrimidin-4(5H)-one;
5-amino-3-(((2R,3R)-2,3,4-trihydroxybutylamino)methyl)-
1H-pyrazolo[4,3-d]pyrimidin-7(6H)-one;
5-amino-3-(((2S,3 S)-2,3,4-trihydroxybutylamino)methyl)-
1H-pyrazolo[4,3-d]pyrimidin-7(6H)-one;
5-amino-3-(((2R,3 S)-2,3,4-trihydroxybutylamino)methyl)-
1H-pyrazolo[4,3-d]pyrimidin-7(6H)-one;
5-amino-3-(((2S,3R)-2,3,4-trihydroxybutylamino)methyl)-
1H-pyrazolo[4,3-d]pyrimidin-7(6H)-one;
7-((benzyl((2R3R)-3,4-dihydroxy-2-(methylthiomethyl)
butyl)amino)methyl)-3H-pyrrolo[3,2-d]pyrimidin-4(5H)-
one;
7-((benzyl((2 S,3 S)-3,4-dihydroxy-2-(methylthiomethyl)
butyl)amino)methyl)-3H-pyrrolo[3,2-d]pyrimidin-4(5H)-
one;
7-((benzyl((2R,3 S)-3,4-dihydroxy-2-(methylthiomethyl)
butyl)amino)methyl)-3H-pyrrolo[3,2-d]pyrimidin-4(6H)-
one;
7-((benzyl((2S,3 S)-3,4-dihydroxy-2-(methylthiomethyl)
butyl)amino)methyl)-3H-pyrrolo[3,2-d]pyrimidin-4(5H)-
one;
2-amino-7-((benzyl((2R,3R)-3,4-dihydroxy-2-(methylthio-
methyl)butyl)amino)methyl)-3H-pyrrolo[3,2-d]pyrimi-
din-4(5H)-one;
2-amino-7-((benzyl((2S,3 S)-3,4-dihydroxy-2-(methylthio-
methyl)butyl)amino)methyl)-3H-pyrrolo[3,2-d]pyrimi-
din-4(5H)-one;
2-amino-7-((benzyl((2R,3 S)-3,4-dihydroxy-2-(methylthio-
methyl)butyl)amino)methyl)-3H-pyrrolo[3,2-pyrimidin-4
(5H)-one;
2-amino-7-((benzyl((2S,3R)-3,4-dihydroxy-2-(methylthio-
methyl)butyl)amino)methyl)-3H-pyrrolo[3,2-d]pyrimi-
din-4(5H)-one;
(S)-7-(1-(1,3-dihydroxypropan-2-ylamino)-2-hydroxy-
ethyl)-3H-pyrrolo[3,2-d]pyrimidin-4(5H)-one;
(R)-7-(1-(1,3-dihydroxypropan-2-ylamino)-2-hydroxy-
ethyl)-3H-pyrrolo[3,2-d]pyrimidin-4(5H)-one;
(S)-2-amino-7-(1-(1,3-dihydroxypropan-2-ylamino)-2-hy-
droxyethyl)-3H-pyrrolo[3,2-d]pyrimidin-4(5H)-one;
(R)-2-amino-7-(1-(1,3-dihydroxypropan-2-ylamino)-2-hy-
droxyethyl)-3H-pyrrolo[3,2-d]pyrimidin-4(5H)-one;
(S)-3-(1-(1,3-dihydroxypropan-2-ylamino)-2-hydroxy-
ethyl)-1H-pyrazolo[4,3-d]pyrimidin-7(6H)-one;
(R)-3-(1-(1,3-dihydroxypropan-2-ylamino)-2-hydroxy-
ethyl)-1H-pyrazolo[4,3-d]pyrimidin-7(6H)-one;
7-(((2R,3R)-2,3-dihydroxy-4-(methylthio)butylamino)
methyl)-3H-pyrrolo[3,2-d]pyrimidin-4(5H)-one;
7-(((2S,3 S)-2,3-dihydroxy-4-(methylthio)butylamino)
methyl)-3H-pyrrolo[3,2-d]pyrimidin-4(5H)-one;
7-(((2R,3 S)-2,3-dihydroxy-4-(methylthio)butylamino)
methyl)-3H-pyrrolo[3,2-d]pyrimidin-4(5H)-one;
7-(((2S,3R)-2,3-dihydroxy-4-(methylthio)butylamino)
methyl)-3H-pyrrolo[3,2-d]pyrimidin-4(5H)-one;
2-amino-7-(((2R,3R)-2,3-dihydroxy-4-(methylthio)buty-
lamino)methyl)-3H-pyrrolo[3,2-d]pyrimidin-4(5H)-one;
2-amino-7-(((2S,3 S)-2,3-dihydroxy-4-(methylthio)buty-
lamino)methyl)-3H-pyrrolo[3,2-d]pyrimidin-4(5H)-one;
2-amino-7-(((2R,3 S)-2,3-dihydroxy-4-(methylthio)buty-
lamino)methyl)-3H-pyrrolo[3,2-d]pyrimidin-4(5H)-one;
2-amino-7-(((2S,3R)-2,3-dihydroxy-4-(methylthio)buty-
lamino)methyl)-3H-pyrrolo[3,2-d]pyrimidin-4(5H)-one;
(R)-7-((benzyl(2,3-dihydroxypropyl)amino)methyl)-3H-
pyrrolo[3,2-d]pyrimidin-4(5H)-one;
(S)-7-((benzyl(2,3-dihydroxypropyl)amino)methyl)-3H-
pyrrolo[3,2-d]pyrimidin-4(5H)-one;
(R)-2-amino-7-((benzyl(2,3-dihydroxypropyl)amino)
methyl)-3H-pyrrolo[3,2-d]pyrimidin-4(5H)-one;
(S)-2-amino-7-((benzyl(2,3-dihydroxypropyl)amino)
methyl)-3H-pyrrolo[3,2-d]pyrimidin-4(5H)-one;
(R)-3-((2,3-dihydroxypropylamino)methyl)-1H-pyrazolo[4,
3-d]pyrimidin-7(6H)-one;
(S)-3-((2,3-dihydroxypropylamino)methyl)-1H-pyrazolo[4,
3-d]pyrimidin-7(6H)-one;
(R)-7-(((2,3-dihydroxypropyl)(2-hydroxyethyl)amino)
methyl)-3H-pyrrolo[3,2-d]pyrimidin-4(5H)-one;
(S)-7-(((2,3-dihydroxypropyl)(2-hydroxyethyl)amino)
methyl)-3H-pyrrolo[3,2-d]pyrimidin-4(5H)-one;
(R)-2-amino-7-(((2,3-dihydroxypropyl)(2-hydroxyethyl)
amino)methyl)-3H-pyrrolo[3,2-d]pyrimidin-4(5H)-one;
(S)-2-amino-7-(((2,3-dihydroxypropyl)(2-hydroxyethyl)
amino)methyl)-3H-pyrrolo[3,2-d]pyrimidin-4(5H)-one;
(R)-3-(((2,3-dihydroxypropyl)(2-hydroxyethyl)amino)
methyl)-1H-pyrazolo[4,3-d]pyrimidin-7(6H)-one;
(S)-3-(((2,3-dihydroxypropyl)(2-hydroxyethyl)amino)
methyl)-1H-pyrazolo[4,3-d]pyrimidin-7(6H)-one;
(2R,3R)-7-((3,4-dihydroxy-2-(hydroxymethyl)butylamino)
methyl)-3H-pyrrolo[3,2-d]pyrimidin-4(5H)-one;
(2S,3 S)-7-((3,4-dihydroxy-2-(hydroxymethyl)butylamino)
methyl)-3H-pyrrolo[3,2-d]pyrimidin-4(5H)-one;
(2R,3 S)-7-((3,4-dihydroxy-2-(hydroxymethyl)butylamino)
methyl)-3H-pyrrolo[3,2-d]pyrimidin-4(5H)-one;
(2S,3R)-7-((3,4-dihydroxy-2-(hydroxymethyl)butylamino)
methyl)-3H-pyrrolo[3,2-d]pyrimidin-4(5H)-one;
(2R,3R)-2-amino-7-((3,4-dihydroxy-2-(hydroxymethyl)
butylamino)methyl)-3H-pyrrolo[3,2-d]pyrimidin-4(5H)-
one;

(2S,3S)-2-amino-7-((3,4-dihydroxy-2-(hydroxymethyl)butylamino)methyl)-3H-pyrrolo[3,2-d]pyrimidin-4(5H)-one;
(2R,3S)-2-amino-7-((3,4-dihydroxy-2-(hydroxymethyl)butylamino)methyl)-3H-pyrrolo[3,2-d]pyrimidin-4(5H)-one;
(2S,3R)-2-amino-7-((3,4-dihydroxy-2-(hydroxymethyl)butylamino)methyl)-3H-pyrrolo[3,2-d]pyrimidin-4(5H)-one;
(2R,3R)-5-amino-3-((3,4-dihydroxy-2-(hydroxymethyl)butylamino)methyl)-1H-pyrazolo[4,3-d]pyrimidin-7(6H)-one;
(2S,3S)-5-amino-3-((3,4-dihydroxy-2-(hydroxymethyl)butylamino)methyl)-1H-pyrazolo[4,3-d]pyrimidin-7(6H)-one;
(2R,3S)-5-amino-3-((3,4-dihydroxy-2-(hydroxymethyl)butylamino)methyl)-1H-pyrazolo[4,3-d]pyrimidin-7(6H)-one;
(2S,3R)-5-amino-3-((3,4-dihydroxy-2-(hydroxymethyl)butylamino)methyl)-1H-pyrazolo[4,3-d]pyrimidin-7(6H)-one;
7-(((2R,3R)-3,4-dihydroxy-1-(methylthio)butan-2-ylamino)methyl)-3H-pyrrolo[3,2-d]pyrimidin-4(5/7)-one;
7-(((2S,3S)-3,4-dihydroxy-1-(methylthio)butan-2-ylamino)methyl)-3H-pyrrolo[3,2-d]pyrimidin-4(5H)-one;
7-(((2R,3S)-3,4-dihydroxy-1-(methylthio)butan-2-ylamino)methyl)-3H-pyrrolo[3,2-d]pyrimidin-4(5H)-one;
7-(((2S,3R)-3,4-dihydroxy-1-(methylthio)butan-2-ylamino)methyl)-3H-pyrrolo[3,2-d]pyrimidin-4(5H)-one;
2-amino-7-(((2R,3R)-3,4-dihydroxy-1-(methylthio)butan-2-ylamino)methyl-3H-pyrrolo[3,2-d]pyrimidin-4(5H)-one;
2-amino-7-(((2S,3S)-3,4-dihydroxy-1-(methylthio)butan-2-ylamino)methyl)-3H-pyrrolo[3,2-d]pyrimidin-4(5H)-one;
2-amino-7-(((2R,3S)-3,4-dihydroxy-1-(methylthio)butan-2-ylamino)methyl)-3H-pyrrolo[3,2-d]pyrimidin-4(5H)-one;
2-amino-7-(((2S,3R)-3,4-dihydroxy-1-(methylthio)butan-2-ylamino)methyl)-3H-pyrrolo[3,2-d]pyrimidin-4(5H)-one;
3-(((2R,3R)-3,4-dihydroxy-1-(methylthio)butan-2-ylamino)methyl)-1H-pyrazolo[4,3-d]pyrimidin-7(6H)-one;
2-(((2R,3R)-3,4-dihydroxy-1-(methylthio)butan-2-ylamino)methyl)-1H-pyrazolo[4,3-d]pyrimidin-7(6H)-one;
3-(((2R,3S)-3,4-dihydroxy-1-(methylthio)butan-2-ylamino)methyl)-1H-pyrazolo-[4,3-d]pyrimidin-7(6H)-one;
3-(((2S,3R)-3,4-dihydroxy-1-(methylthio)butan-2-ylamino)methyl)-1H-pyrazolo[4,3-d]pyrimidin-7(6H)-one;
3-(((2R,3R)-3,4-dihydroxy-2-(methylthiomethyl)butylamino)methyl)-1H-pyrazolo[4,3-d]pyrimidin-7(6H)-one;
3-(((2S,3S)-3,4-dihydroxy-2-(methylthiomethyl)butylamino)methyl)-1H-pyrazolo[4,3-d]pyrimidin-7(6H)-one;
3-(((2R,3S)-3,4-dihydroxy-2-(methylthiomethyl)butylamino)methyl)-1H-pyrazolo[4,3-d]pyrimidin-7(6H)-one;
3-(((2S,3R)-3,4-dihydroxy-2-(methylthiomethyl)butylamino)methyl)-1H-pyrazolo[4,3-d]pyrimidin-7(6H)-one;
2-amino-7-(((2R,3R)-3,4-dihydroxy-2-(methylthiomethyl)butylamino)methyl)-3H-pyrrolo[3,2-d]pyrimidin-4(5H)-one;
2-amino-7-(((2S,3S)-3,4-dihydroxy-2-(methylthiomethyl)butylamino)methyl)-3H-pyrrolo[3,2-d]pyrimidin-4(5H)-one;
2-amino-7-(((2R,3S)-3,4-dihydroxy-2-(methylthiomethyl)butylamino)methyl)-3H-pyrrolo[3,2-d]pyrimidin-4(5H)-one;
2-amino-7-(((2S,3R)-3,4-dihydroxy-2-(methylthiomethyl)butylamino)methyl)-3H-pyrrolo[3,2-d]pyrimidin-4(5H)-one;
7-(((2R,3R)-3,4-dihydroxy-2-(methy[thiomethyl)butylamino)methyl)-3H-pyrrolo[3,2-d]pyrimidin-4(5H)-one;
7-(((2S,3S)-3,4-dihydroxy-2-(methylthiomethyl)butylamino)methyl)-3H-pyrrolo[3,2-d]pyrimidin-4(5H)-one;
7-(((2R,3S)-3,4-dihydroxy-2-(methylthiomethyl)butylamino)methyl-3H-pyrrolo[3,2-d]pyrimidin-4(5H)-one; or
7-(((2S,3R)-3,4-dihydroxy-2-(methylthiomethyl)butylamino)methyl)-3H-pyrrolo[3,2-d]pyrimidin-4(5H)-one.

75. A compound of formula (VI):

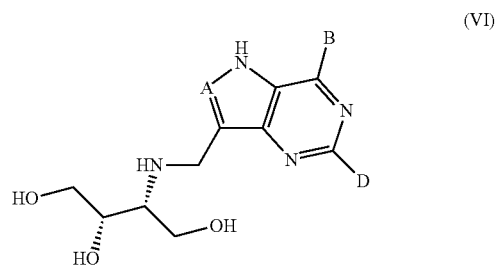

(VI)

where A is N or CH; B is OH or alkoxy; and D is H, OH, $NH_2$, or $SCH_3$.

76. The compound (2S,3R)-3-((4-hydroxy-5H-pyrrolo[3,2-d]pyrimidin-7-yl)-methylamino)butane-1,2,4-triol having the formula:

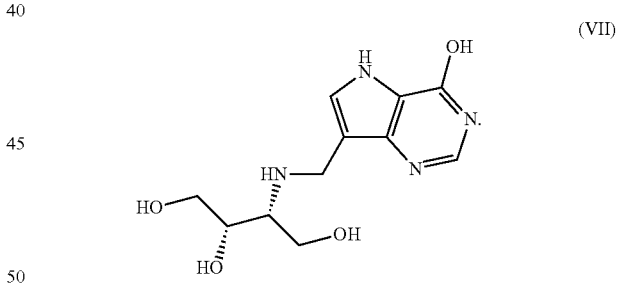

(VII)

As a further aspect, the invention provides pharmaceutical formulations and methods of administering the same to achieve any of the therapeutic effects (e.g., inhibition of lung inflammation) discussed above. The pharmaceutical formulation may comprise any of the agents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science*

*And Practice of Pharmacy* (22nd Ed. 2012). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

A further aspect of the invention is a method of treating subjects in vivo, comprising administering to a subject a pharmaceutical composition comprising a compound of the invention in a pharmaceutically acceptable carrier, wherein the pharmaceutical composition is administered in a therapeutically effective amount. Administration of the compounds of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and nasal and/or oral inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis/tris buffer (pH 6) or ethanol/water and contain from 0.1 to 0.2M of the compound.

The compound can alternatively be formulated for nasal and/or oral administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990)

Critical Reviews in Therapeutic Drug Carrier Systems 6:273-313; and Raeburn et al., J. Pharmacol. Toxicol. Meth. 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., Remington's Pharmaceutical Sciences (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic and/or prophylactic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, adults and geriatric subjects.

In particular embodiments, the subject is a human subject that has a lung disease associated with inflammation. In other embodiments, the subject used in the methods of the invention is an animal model of a lung disease associated with inflammation.

The subject can be a subject "in need of" the methods of the present invention, e.g., in need of the therapeutic or prophylactic effects of the inventive methods. For example, the subject can be a subject that is experiencing a lung disease associated with inflammation and/or is anticipated to experience a lung disease associated with inflammation, and the methods and compositions of the invention are used for therapeutic and/or prophylactic treatment.

The present invention is more particularly described in the following examples that are intended as illustrative only since numerous modifications and variations therein will be apparent to those skilled in the art.

Example 1

MTA Modulates Inflammatory Response

The potent anti-inflammatory profile of MTA has been demonstrated in a number of models. In lipopolysaccharide (LPS) challenged mice, MTA markedly reduced serum levels of the pro-inflammatory tumor necrosis factor-alpha (TNF-α) and stimulated production of the anti-inflammatory cytokine interleukin-10. Cell based LPS inflammation models have shown MTA to inhibit induction of p38 Mitogen Activated Protein Kinase (MAPK), c-Jun phosphorylation and Inhibitors of Kappa Balpha (IKBα) degradation. Concomitant reduction of Nuclear Factor-KB (NFKB) activation was also observed. Each of these pathways is associated with the modulation of inflammatory mediators and supports the role of MTA as promoting an anti-inflammatory state. A rat model of ischemia/reperfusion injury following liver transplant emulates the LPS results with notable suppression of NFKB and MAPK pathways observed. The use of MTA alone as a therapeutic for CF has limited utility because of pharmacokinetics (PK). MTAP rapidly metabolizes MTA in vivo with excess MTA cleared renally, as demonstrated by high urine concentrations of MTA in exploratory PK experiments.

Example 2

MTDIA Blocks MTA Metabolism at MTAP

Oral doses of MTDIA block MTA metabolism at MTAP, which causes whole-body accumulation of MTA and simultaneous disruption of polyamine synthesis (FIG. 3). MTDIA inhibits MTAP, the sole enzyme responsible for MTA recycling, with picomolar affinity and a high level of specificity. An oral or i.p. dose of MTDIA inhibits MTAP activity in vivo for >24 h, causes MTA accumulation in plasma to >100-fold higher than baseline levels and ~2-fold decrease in polyamine concentrations.

MTDIA was designed and synthesized as a chemically stable analogue for the proposed transition state of human MTAP (Ki*=86 μM). MTDIA has high specificity and affinity for MTAP, displaying minimal off-target effects in protein receptor and kinase panels. Therapeutically relevant concentrations (FIG. 7A) of MTDIA (100 μM) or MTA (1.2 μM) returned selectivity (S) scores of 0 and 0.008 (S=number of hits/number of assays) respectively in a KINOMEscan™ kinase screening assay against 456 human kinases and disease relevant mutants, indicating minimal off-target binding. Hits were calculated at the lowest stringency permitted in the assay, indicating the absence of significant kinase inhibition. MTDIA is also highly soluble in aqueous media (156 mM in PBS), orally available, and metabolically stable in microsomes and hepatocytes. No significant toxicity has been observed in all in vitro (2D and 3D culture studies) and in vivo studies performed to date.

Example 3

MTDIA Pharmacokinetics (PK)/Pharmacodynamics (PD)

Figure 7A:
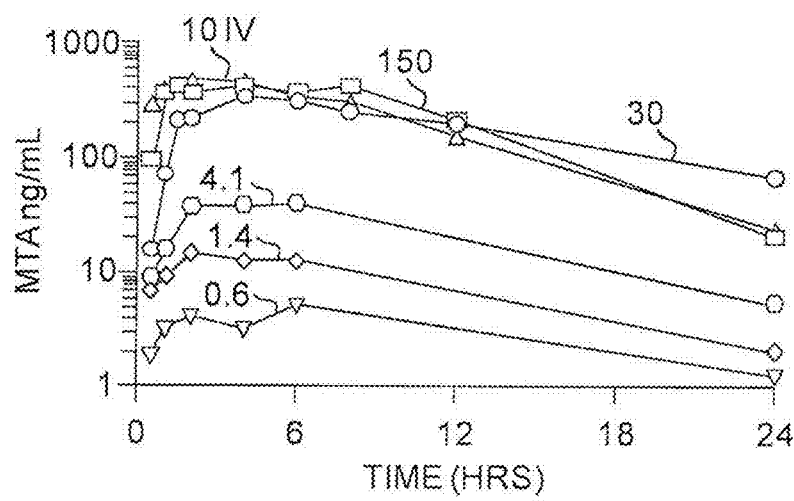
FIGS. 7A-7C show PK and PD of single dose oral MTDIA. A) Serum MTA concentrations after single oral dose of various concentrations of MTDIA (range 0.6-150 mg/kg, numbers on graph represent dose in mg/kg MTDIA) as well as a 10 mg/kg dose IV. Single oral doses of MTDIA yield increased serum MTA concentrations, with maximum effect at 30 mg/kg in this experiment. Similar increases in MTA were observed at 15 mg/kg in a separate study. B) A single dose of 15 mg/kg MTDIA increases serum MTA in both WT and Scnn1b-Tg (Beta) mice at 24 hours. C) Similar increases in MTA were observed in BALF after MTDIA treatment.

Following an oral or i.p. dose (15 mg/kg) in CD-1 mice, the concentration of MTDIA in plasma peaks after 1 hr at nearly 0.1 μM (FIG. 7A). This concentration is approximately 1,000-fold higher than the Ki* of MTDIA (86 pM) for human MTAP. MTDIA (15 mg/kg) causes plasma MTA levels in mice to increase >100-fold (FIG. 7B) after 30 min, and urinary MTA to increase to approximately 30 μM. The catalytic activity of MTAP in mouse serum is completely inhibited for 24 hr after a single oral dose (15 mg/kg) and returns to normal within 36 hr. MTDIA was found to be metabolically stable for over 4 hr during in vitro studies with human hepatocytes and microsomes. These findings demonstrate that MTDIA is orally available and metabolically stable.

Example 4

MTDIA Toxicology

In CD-1 mice, a single dose of MTDIA was administered by gavage to establish acute toxicity (300, 600 and 1000 mg/kg), or once daily for seven consecutive days (0, 600 and 1000 mg/kg/day) to determine repeat-dose toxicity. Mice were monitored for abnormalities, survival rates, histopathological changes (heart, lung, liver, kidney, spleen, small intestine and stomach were evaluated histopathologically by a board certified pathologist), clinical chemistry and complete blood count (CBC) analysis. No drug related changes in mortality, hematology, or clinical signs of toxicity were observed. The LOAEL (Lowest-Observed-Adverse-Effect level) was established at 600 mg/kg/day. The NOAEL (No-Observed-Adverse-Effect-Level) was not established under in this study. No histopathological findings were detected in any study arm.

Example 5

Identification of the Methionine Salvage Pathway by Transcriptomic and Metabolomics Analyses Untargeted genomic studies suggested a relationship between the methionine salvage pathway and lung disease progression in CF. As a part of the ongoing efforts to complement genome-wide association studies (GWAS) studies, we have been involved in a long-standing project to evaluate gene expression associations with disease phenotype. Recently, we performed a transcriptomic analysis of gene expression, based on RNA sequencing, of nasal epithelia obtained from CF patients in relation to a cross-sectional normalized measure of lung disease (SakNorm (Taylor et al., Pediatr. Pulmonol. 46:857 (2011))). In a sample set from 133 CF patients, representing a subset of the GWAS cohort, pathway analysis using a highly rigorous permutation-based approach (SAFE, developed by Fred Wright (Barry et al., Bioinformatics 21:1943 (2005))) identified the methionine salvage pathway as one of several pathways significantly associated with lung disease severity with a FDR q-value <0.10. Interestingly, in this analysis, not only was the association with the pathway itself significant, but two individual genes annotated to the pathway, AMD1 (p<0.01) and MTAP (p<0.10) showed individually significant associations, with expression of APIP and other genes contributing to the overall significance of the pathway (Table 1). Thus, transcriptomic gene expression studies provide a highly robust, independent identification of a relationship between the methionine salvage pathway and lung function.

TABLE 1

Genes associated with SakNorm; methionine salvage pathway

| Gene | Local Stat* | P-value |
|------|-------------|---------|
| AMD1 | −2.708 | 0.0080 |
| MTAP | −1.790 | 0.0822 |
| MAT2B | −1.159 | 0.2451 |
| APIP | −1.081 | 0.2762 |

*negative = increased with worse lung disease

Figure 4A:
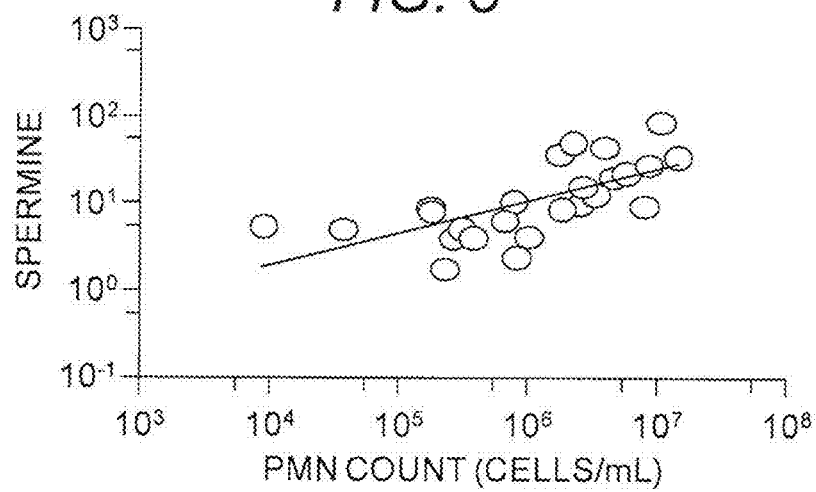
FIGS. 4A-4D show findings in CF bronchoalveolar lavage fluid (BALF). In BALF from children with CF, the polyamine spermine and MTA product adenine are associated with neutrophil (PMN) counts (A, B), and (C) elevated in samples with pathogens (shaded) vs. those without (open). (D) Spermine is also correlated with lung function measured as percent predicted Forced Expiratory Volume in 1 second ($FEV_1$).
Figure 4B:
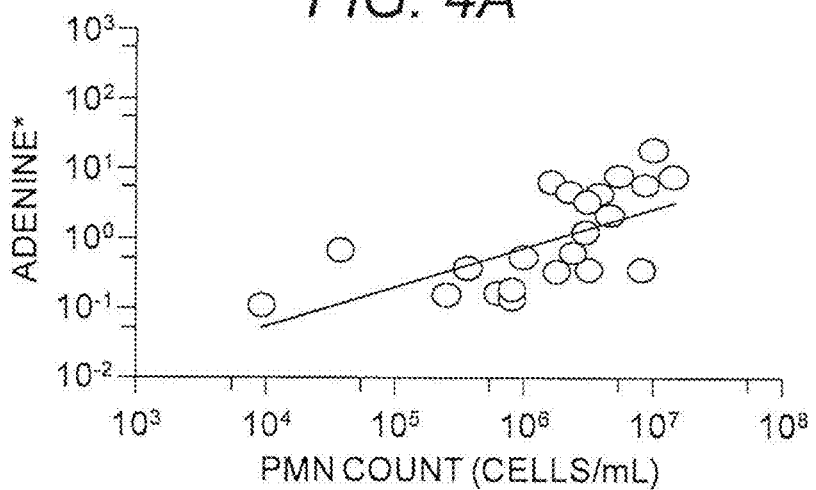
Figure 4C:
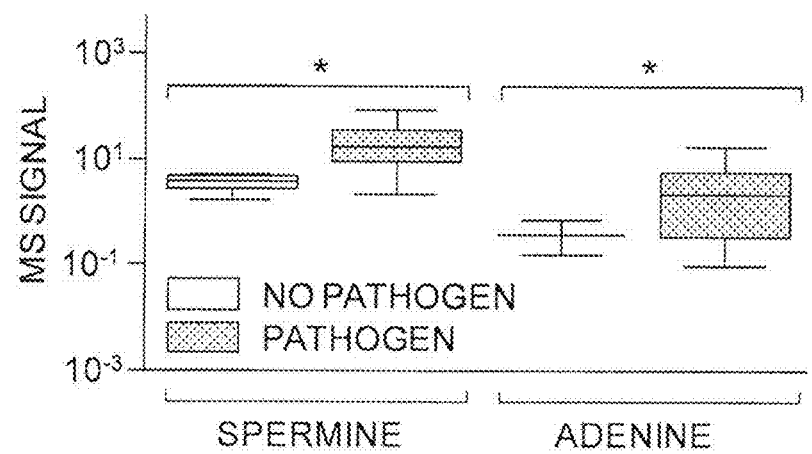
Figure 4D:
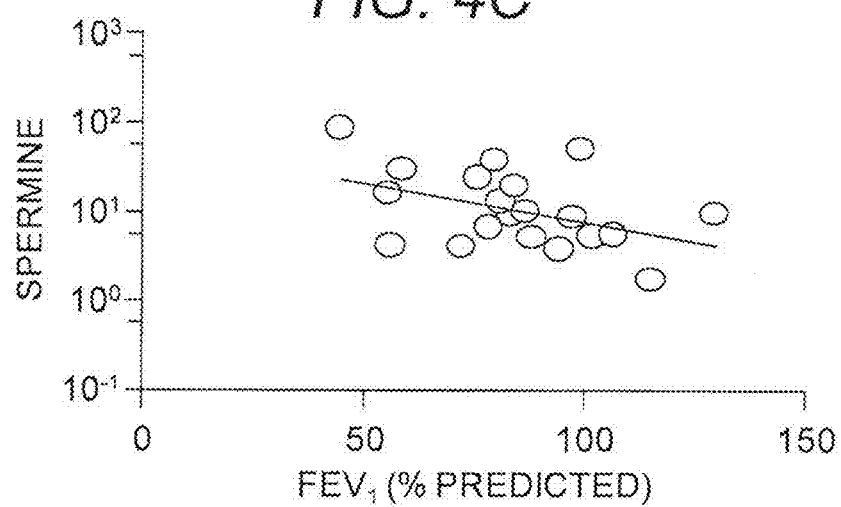

Metabolomics studies provide further evidence of a role for the methionine salvage pathway in CF lung disease. We recently utilized a mass spectrometric (MS) based metabolomics approach to identity metabolites associated with neutrophilic airway inflammation in bronchoalveolar lavage fluid (BALF) from children with CF and developed a targeted MS method that could be used to quantify these metabolites in various samples (Esther et al., Am. J. Respir. Crit. Care Med. 187:A1165 (2013)). In these studies, several polyamines including spermine, spermidine, and putrescine were positively correlated with BALF neutrophil counts, as was adenine (a product of MTA hydrolysis) (FIGS. 4A-4B). In addition to being correlated with neutrophils, spermine and adenine were also elevated in samples with pathogens identified on BALF culture (FIG. 4C), and spermine was inversely correlated with lung function (FIG. 4D). These findings demonstrate that metabolites reflective of increased activity of the methionine salvage pathway are also increased in airways inflammation in CF, further supporting a role for this pathway in progression of airways disease. Interestingly, we observed similar increased in polyamines in airway samples from subjects with COPD (not shown), and others have reported elevated airway polyamines in asthma (Kurosawa et al., *Allergy* 47:638 (1992)) suggesting that the relationship between methionine salvage pathway and airway inflammation is not CF specific.

Figure 5:
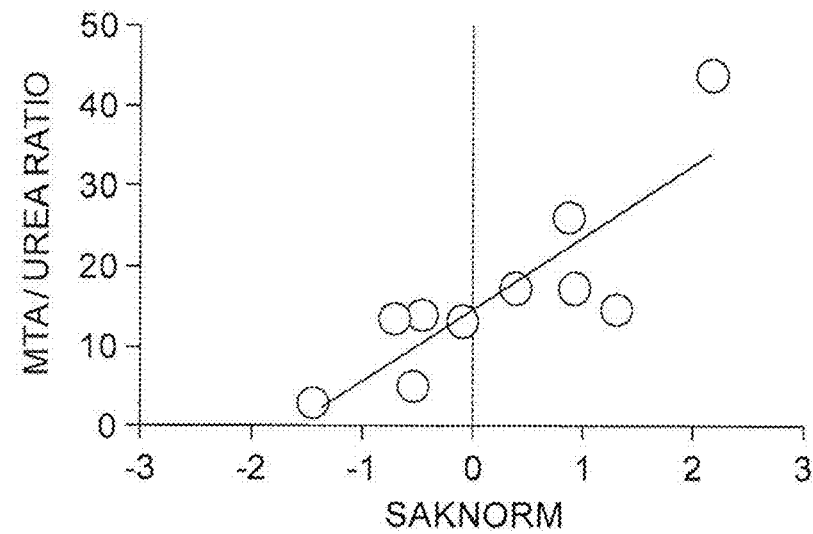
FIG. 5 shows MTA detection in airway secretions. MTA in nasal lavage correlated with the SakNorm measure of lung disease severity (n=10, r=0.84, p<0.002). Ratios to urea were utilized to control for variable dilution of nasal secretions during lavage. Negative values of the Local.Stat measure indicate higher expression levels in subjects with greater disease severity.

Since the relationship between lung disease and the methionine salvage pathway is likely driven by changes in MTA concentrations, we developed a MS method to measure this compound directly. MTA was detected as a single peak at a run time of ~6.0 minutes in liquid chromatography-tandem mass spectrometry (LC-MS/MS) in both standard solution and airway samples. Application of this method to nasal lavages obtained during the nasal epithelial gene expression study described above revealed a positive correlation between nasal lavage MTA concentrations and the SakNorm normalized measure of lung disease (FIG. 5), when variations in nasal lavage were controlled through ratios to the dilution marker urea. This study demonstrates the same inverse relationship between MTA concentrations and lung disease severity predicted from the other 'omics studies.

Example 6

Methionine Salvage Pathway and Lung Disease in Model Systems

The above findings suggest that pharmacological agents such as MTDIA that block the methionine salvage pathway could act as anti-inflammatory therapies for the chronic airways inflammation observed in CF. We sought to test this hypothesis in an animal model, but since the CF mouse does not develop spontaneous airways disease (Davidson et al., *Exp. Rev. Molecular Med.* 2001:1 (2001)), we initially chose to study the Scnn1b-Tg mouse. This mouse, also known as the Beta mouse, overexpresses the beta subunit of the ENaC sodium channel and develops airway fluid dehydration and lung disease with features similar to CF, including reduced mucociliary clearance, mucus plugging, and chronic neutrophilic inflammation (Mall et al., *Am. J. Respir. Crit. Care Med.* 177(7):730 (2008)). The model has been extensively used to explore factors that interact with innate immunity in the context of airway surface dehydration, including preclinical testing of novel pharmacological agents that target CF airway inflammation.

Figure 6A:
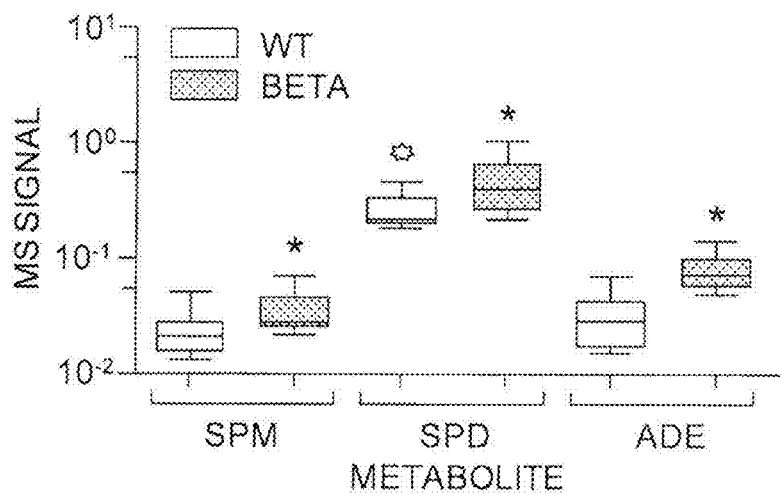
FIGS. 6A-6C show findings in Scnn1b-Tg mouse airways. A) The polyamines spermine (Spm) and spermidine (Spd) as well as adenine (Ade) were elevated in BALF from adult Scnn1b-Tg mice relative to wild-type controls (n=10/group). B) Ade correlated with BALF neutrophil counts. C) Ade was elevated and MTA decreased in airway samples form week old Scnn1b-Tg mice relative to wild-type (n=4/group).
Figure 6B:
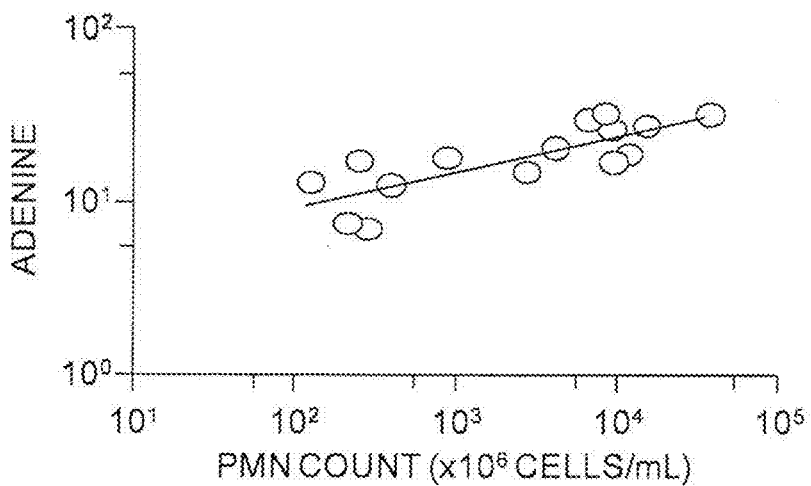
Figure 6C:
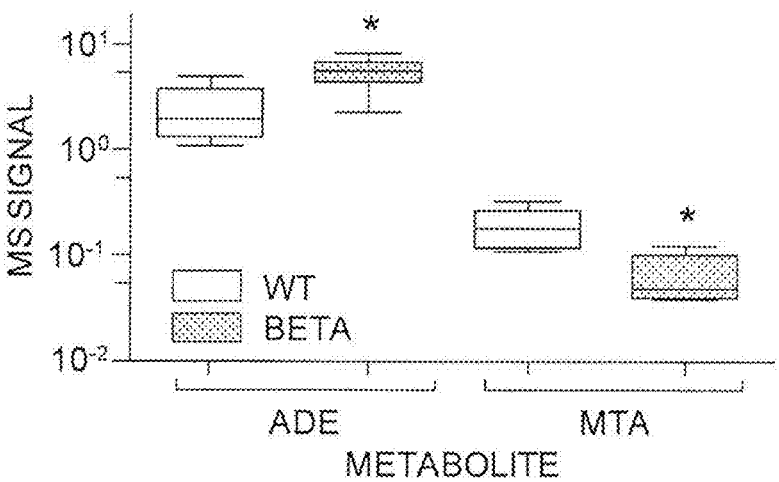

In our initial experiments, we used our MS methods on BALF obtained from adult Scnn1b-Tg (Beta) mice and demonstrated elevated concentrations of polyamines and adenine in BALF, as well as correlations between adenine and neutrophil counts (FIGS. 6A and 6B) similar to findings in human CF. In a subsequent experiment performed after MTA detection was added to the MS method, we confirmed that BALF adenine concentrations were elevated in Beta mice and that BALF MTA concentrations were lower (FIG. 6C). These patterns are all consistent with elevated activity of the methionine salvage pathway in this mouse model.

Example 7

MTDIA Treatment in Mouse Models

Figure 7B:
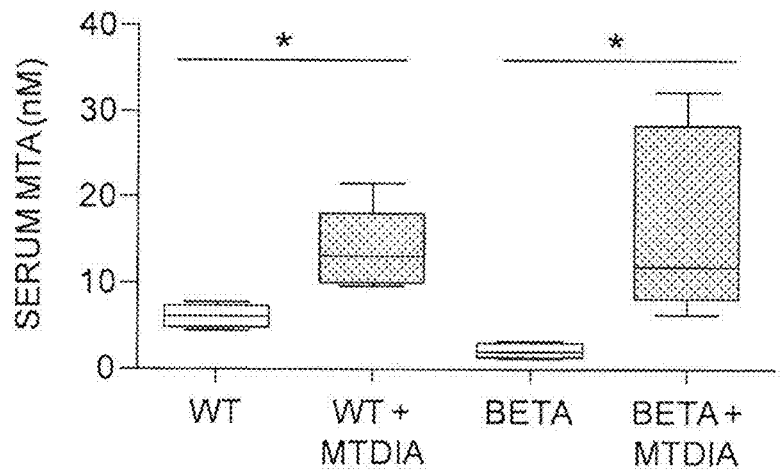
Figure 7C:
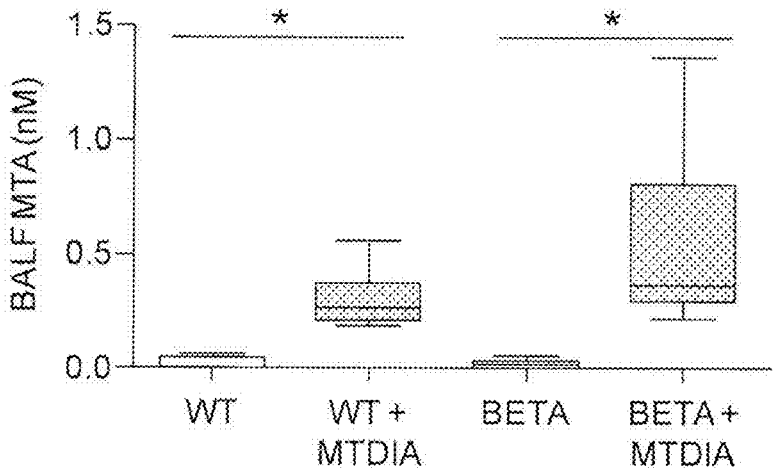

Having demonstrated that the methionine salvage pathway appears elevated in the Scnn1b-Tg mouse, we next explored the effects of MTDIA treatment. Previous experiments had suggested that 15 mg/kg oral dose of MTDIA yielded a maximal response in serum MTA concentrations (FIG. 7A). We verified that a single 15 mg/kg dose given by oral gavage resulted in an increase in serum MTA concentrations after 24 hours in both wild type (WT) and Scnn1b-Tg mice (FIG. 7B). Similar increases in MTA were observed in BALF (FIG. 7C), though we did not observe any changes in BALF inflammatory markers after a single dose.

Figure 8A:
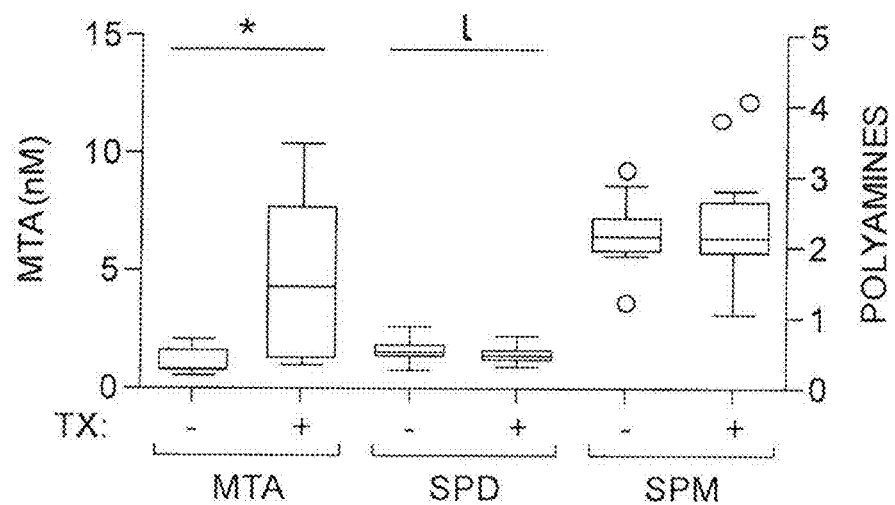
FIGS. 8A-8C show 3 days oral MTDIA. A) Daily oral gavage of 15 mg/kg MTDIA over three days in Scnn1b-Tg mice results in increased serum MTA concentrations in MTDIA treated (n=13) vs. vehicle treated (n=11) mice, though minimal changes in free spermidine (Spd) or spermine (Spm). B) Similar changes were observed in BALF after three days of MTDIA treatment. C) Cell counts of neutrophils (PMNs) and eosinophils (Eos) were reduced after three days of MTDIA treatment relative to controls, with a corresponding increase in macrophages (Macs).
Figure 8B:
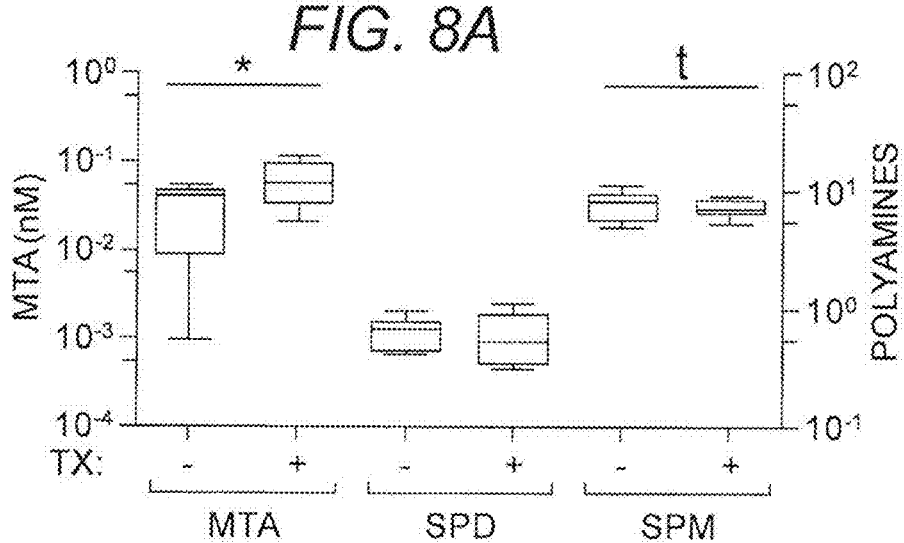

Previous studies of anti-inflammatory agents in the Scnn1b-Tg mouse suggested that beneficial effects could be seen with repeated dosing (Hardy et al., *Immunol. Cell Biol.* 93:567 (2015); Galluzzo et al., *Mediators Inflammation* 2015:545417 (2015)). Therefore, we repeated the above study in Scnn1b-Tg mice using 15 mg/kg MTDIA by oral gavage once daily for three days. With the longer treatment, we observed increases in serum (FIG. 8A) and BALF (FIG. 8B) MTA concentrations in treated mice relative to vehicle treated animals (n=13 and 11, respectively), similar to the changes seen with the single dose experiments. Although increased concentrations of MTA can reduce polyamine synthesis, we did not observe large changes in the free concentrations polyamines spermine (Spm) and spermidine (Spd) in serum or BALF, though these results should be interpreted with caution since we did not examine polyamine concentrations in cell membranes.

Figure 8C:
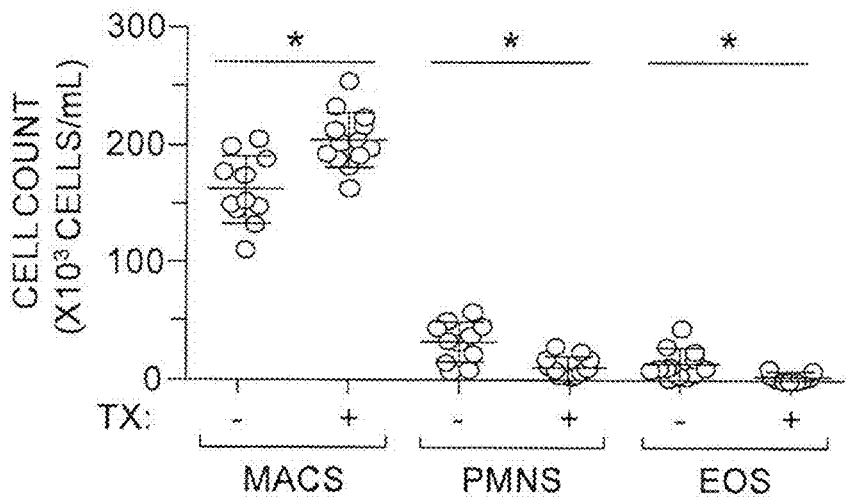

More importantly, we observed that three days of oral MTDIA treatment led to a significant reduction in the cell counts of both neutrophils (32.0+16.9 vs. 11.5+8.2×10$^3$ cells/ml, $p<0.001$) and eosinophils (14.2+13.5 vs. 2.2+3.2×10$^3$ cells/ml, $p<0.001$), with a corresponding increase in macrophage cell counts (FIG. 8C). Similar differences were observed when BALF inflammatory cells were analyzed as cell differentials rather than cell counts. These findings provide compelling evidence that MTDIA can act as an anti-inflammatory drug in a chronic airways disease model.

The findings from the mouse model studies strongly support the evidence from the genomic, transcriptomic, and metabolomic studies, all of which strongly implicate the methionine salvage pathway in development of airway inflammation and lung disease in CF. Critically, the data suggest that variations in the activity of the methionine salvage pathway have a strong influence on progression of lung disease in CF, suggesting that pharmacological modulation of this pathway using MTDIA or similar drugs could be disease altering. Consistent with this hypothesis, MTDIA treatment of the Scnn1b-Tg mouse model results in significant decreases in neutrophilic airway inflammation.

Example 8

Impact of MTDIA on Inflammatory Responses

Studies are performed to determine the therapeutic potential of MTDIA (15 mg/kg) in Cftr deficient mice and evaluate the impact on the inflammatory responses that occur during a CF-relevant bacterial infection. Cftr gut corrected mice (B6.129 Cftr$^{tm1Kth}$ Tg(FABPCFTR)1Jaw/Cwr; gut corrected F508del) are used, as these animals are easy to breed and are cost-effective relative to the Cftr$^{tm1Unc}$ (Cftr-null) or Cftr$^{tm1Kth}$ (F508del). Further, extensive experience has established that the lung response to chronic infection with *Pseudomonas aeruginosa* is similar between the Cftr gut corrected mouse and the other strains, although survival is better due to the lack of gastrointestinal complications. The gut corrected model is also a good control for the moderate survival to sub-lethal dosages of *Pseudomonas aeruginosa*, with animals surviving to determine the impact of the anti-inflammatory agent on pathogen resolution. There are three groups in this study: wild type with infection, Cftr deficient animals with infection, and Cftr deficient animals with infection and drug treatment, Depending upon the outcomes, groups are added to accommodate different dosages, timing or other outcomes if the data support future studies.

Studies are done with males only. The male mice are more robust, potentially requiring changes in dosing, although weight is not a variable since all drugs are administered based upon weight of the animal. Animals are infected with agarose laden beads with $10^5$ CFUs of viable *Pseudomonas aeruginosa* with and without the addition of the therapeutic of question. The groups are followed daily for up to 10 days with a 3-day pull out and day 10 assessment of infection and inflammation resolution.

To look for the impact on inflammation and pathogen resolution, mice undergo BAL. BAL fluid and serum are saved for biomarker evaluation. The standard measurements include bacterial burden, differentials and elastase and the base-line set of CF defined biomarkers: TNFα, IL-1β, IFNγ, KC, MIP-1α, MIP-1β, MCP-1, IL-6, IL-10, IL-17, G-CSF, GM-CSF and calprotectin.

Each group of experiments includes the following groups shown in Table 2.

TABLE 2

| Group # | Genotype | Infection | Treatment/Route | End-point Day 3 | End-point Day 10 |
|---|---|---|---|---|---|
| 1 | WT | PA | Vehicle | N = 10 | N = 10 |
| 2 | CFTR-/- | PA | Vehicle | N = 10 | N = 10 |
| 3 | CFTR-/- | PA | Drug MTDIA (15 mg/kg; oral gavage; once daily) | N = 10 | N = 10 |

Specific study details are as follows.

Day −3: The study is started with validating the *Pseudomonas aeruginosa* culture.

Day −2: The second flask of *Pseudomonas aeruginosa* is started to standardize the growth kinetics and viability of the bacteria.

Day −1: The agarose bead preparation is done incorporating viable $10^5$ *Pseudomonas aeruginosa* into agarose beads with a known size and distribution. These beads are plated to determine success of the procedure prior to giving to the mice.

Day 0: The cultured beads are validated and plotted using CFUs versus titer to determine the quantitative value of the agarose bead preparation. We use this process to identify the $10^5$ CFU dose of *Pseudomonas aeruginosa*. All weights of animal groups are recorded, followed by trans-tracheal administration of agarose bead preparation.

Day 1: The mice are evaluated again for weights and clinical scores. In many cases this will be the start of the administration of therapeutic (single dose, daily dose, BID).

Day 2: Weights and clinical scores are recorded, and therapeutic administration continued if needed.

Day 3: After all of the mice are evaluated for weights, clinical scores, 10 animals are euthanized to evaluate the status of infection and inflammation using bronchoalveolar lavage (BAL). BAL fluid is evaluated for cellular differential, bacterial load and elastase with the remaining fluid aliquoted for biomarker assessment including: TNFα, IL-1β, IFNγ, KC, MIP-1a, MIP-1β, MCP-1, IL-6, IL-10, IL-17, G-CSF, GM-CSF and calprotectin. BAL fluid and cell pellet are kept for future analysis, if deemed reasonable by the study outcome.

Day 4-9: The mice are assessed daily for weights and clinical scores and any indication of adverse effects of the study according to compassionate and reasonable care of animals.

Day 10: Prior to euthanization for BAL, mice (n=10) have their weights and clinical scores recorded, survival will also be documented.

Animals that died during the study are necropsied to determine cause of death. Specifically, lungs, spleen and liver are removed and homogenized for *Pseudomonas aeruginosa* CFUs to look for decompartmentalization of the infection burden. The whole lung, spleen and liver homogenates are kept in two different aliquots. The first for tissue extraction of mRNA and the second for tissue extract for secreted proteins. If data from the study suggests an adverse response to the therapeutic, the whole lung mRNA is evaluated for murine KC, TNFα, IL-6 and MIP-1α. The tissue soluble extract is evaluated using a multiplex format for calprotectin, KC, TNFα, IL-6 and MIP-1α as well as elastase activity. The spleen and liver tissue homogenates are kept for follow-up studies if necessary, looking for stress factors such as C-reactive protein and liver enzymes.

The overall evaluation is to determine the anti-inflammatory effects of MTDIA on the ability of the Cftr deficient lung milieu to manage chronic infection with *Pseudomonas aeruginosa*. The primary parameters in these studies are mortality, weight change and clinical score. The secondary outcomes measured include the lung inflammatory profile and bacteriology, and whether the bacteria has become de-compartmentalized and detectable in the spleen and blood. Based upon our experience, we estimate that approximately 15-20 mice are required to give adequate confidence that the investigational product is not associated with adverse outcomes. On rare occasions, subsequent experiments may be undertaken to increase the N to account for the variability that is seen in in vivo modeling systems. Analyses of log or square-root transformation are used to compare between experimental conditions at a single point with paired t-tests and slopes over time. In the chronic infection models, the survival curves are compared using stratified log-rank tests, using the treatment conditions as strata. Bacterial load, white blood cell counts, and cytokines are log-transformed if necessary and compared between groups or conditions using one or two-way ANOVA, with MTDIA or controls as experimental blocks. Differential counts expressed as percentages are transformed using logit or arcsin (square root) transformations to stabilize variances and better meet normality assumptions. If data cannot be transformed to normality, a nonparametric van-Elteren test is used to compare groups.

Example 9

Determination of Optimal MTDIA Dose

A single oral dose of MTDIA (15 mg/kg) or vehicle control (phosphate buffered saline) is administered to Scnn1b-Tg mice and CF/Scnn1b-Tg mice (a model in which the Scnn1b-Tg mouse has been bred into mice homozygous for the ΔF508 Cftr mutation (Cftr$^{tm1Kth}$)) (n=6/group) and BALF, serum (cardiac puncture), and various tissues (lung, liver, intestine) collected at 24 h. BALF is analyzed by the standard phenotyping CF panel. Airway inflammatory cells (macrophages, neutrophils, lymphocytes, eosinophils) in lavage are counted and BALF inflammatory markers known to be elevated in Scnn1b-Tg mice (KC, MIP2, LIX) are measured in both treated and untreated animals. Utilizing mass spectrometry (MS), Met salvage pathway metabolites including MTA and polyamines are measured in serum, BALF, and tissues of treated Scnn1b-Tg mice and compared to untreated controls. After the initial dose of MTDIA is found to be effective at reducing inflammatory burden, the oral dose is then decreased in increments (15-0.1 mg/kg) to determine the minimum dose required to impart this effect (defined here as the minimum efficacious dose or, MED). MTDIA dose is correlated with Met salvage pathway metabolite levels and subsequent decrease in inflammatory markers.

CF/Scnn1b-Tg and Scnn1b-Tg mice undergo daily oral gavage of MTDIA or vehicle control for 7 days (n=12/group) at the MED, then BALF and serum and tissues are obtained using standard methods at the beginning of day 8 (n=6). Remaining animals (n=6) are monitored for a further 7 days to determine the duration of treatment effects after treatment withdrawal. Inflammatory markers and metabolite levels described for the optimal dose finding study are measured. Based upon the known effect of MTA on LPS-stimulated macrophage function and robust macrophage activation in Scnn1b-Tg mice, markers of macrophage activation (Chi3l3 and Retnla) will also be measured. RNA is saved from all BAL cell pellets to further monitor macrophage activation. For 7-day dosing studies the left lobe is ligated during lavage collections so that histological sections can be obtained from the same animals. Histology features of interest include development of bronchus-associated lymphoid tissue, airway consolidation, mucus plugging, intraluminal mucin production, and pulmonary inflammation. Histological sections also allow identification of unanticipated consequences of long-term MTDIA treatment, such as alveolar consolidation that is seen in the Scnn1b-Tg mice during induced bacterial pneumonia. A 50% reduction in inflammatory markers is the desired therapeutic effect where daily oral doses of MTDIA (<15 mg/kg) cause a statistically significant decrease in airway inflammation in the Scnn1b-Tg mouse for >24 h. Measures include inflammatory cytokines, presence of inflammatory cells, macrophage activation markers and histological parameters associated with inflammatory events. The MED will be preferentially less than 15 mg/kg and a single oral dose will be beneficial for an extended duration (>24 h). A single oral dose of MTDIA reduces airway inflammation in the Scnn1b-Tg mouse, reflected in reduced airway neutrophil counts and reduced TNF-α and KC concentrations. Changes in key inflammatory markers will follow a single dose of MTDIA and an optimal dose will be delivered over a period of several days allowing more significant improvements in inflammatory marker levels to be observed.

Histology features of interest will include development of bronchus-associated lymphoid tissue (BALT), airway consolidation, mucus plugging, intraluminal mucin production, and pulmonary inflammation. In previous experiments with Scnn1b-Tg mice, we have observed that the baseline increased BALT that occurs in this animal (FIGS. 9A-9B) is meaningfully reduced after three days of MTDIA treatment (FIGS. 9C-9D). Histological sections will also allow identification of unanticipated consequences of long-term MTDIA treatment, such as alveolar consolidation that is seen in the Scnn1b-Tg mice during experimentally-induced bacterial pneumonia.

The Scnn1b-Tg mouse is known to have activated macrophages that appear enlarged, and our initial studies suggest that this phenotype appears to be reduced in MTDIA treated animals (FIG. 10). Coupled with the reduced amount of BALT after treatment, this suggests that effects of treatment on neutrophilic inflammation may be mediated by changes in signaling pathways from macrophages and other cell types.

Our data demonstrate that short term treatment with MTDIA can reduce airway neutrophil counts in a mouse model of chronic inflammation, and the PK studies suggest that once daily dosing generates a burst of high MTA concentrations that fades to much lower levels after 24 hours. While consistent with the likely pharmacological use of this drug in human trials, the PK from once daily dosing differs significantly from the naturally occurring variations in methionine salvage pathway activity with smaller, but more consistent chronic changes in MTA concentrations. Experiments are designed to determine if chronic changes in methionine salvage pathway activity that better mimic these natural variations will improve chronic airway inflammation in mouse models.

Figure 11A:
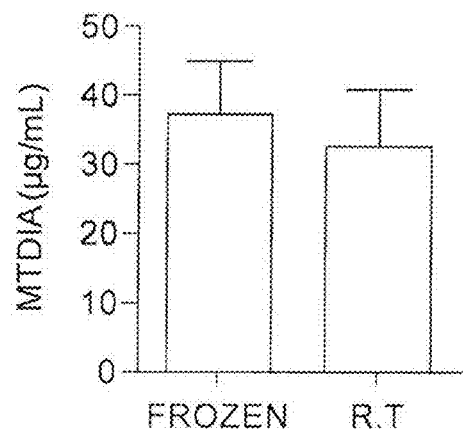
FIGS. 11A-11C show MTDIA in drinking water. A) MTDIA concentrations after three days in drinking water at room temperature (RT) were similar to those in an aliquot frozen directly after preparation. B) WT mice that had 37.5 or 75 µg/mL MTDIA in drinking water had orders of magnitude increases in serum MTA. C) MTDIA in drinking water also increased BALF MTA concentrations (n=5/group).
Figure 11B:
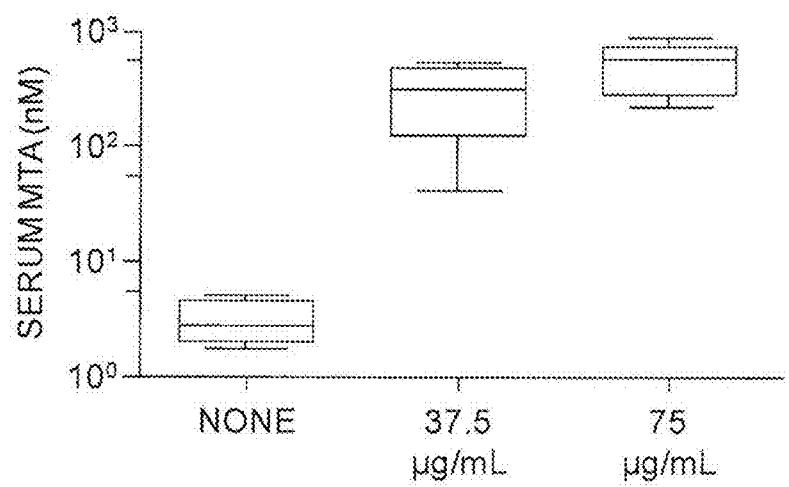
Figure 11C:
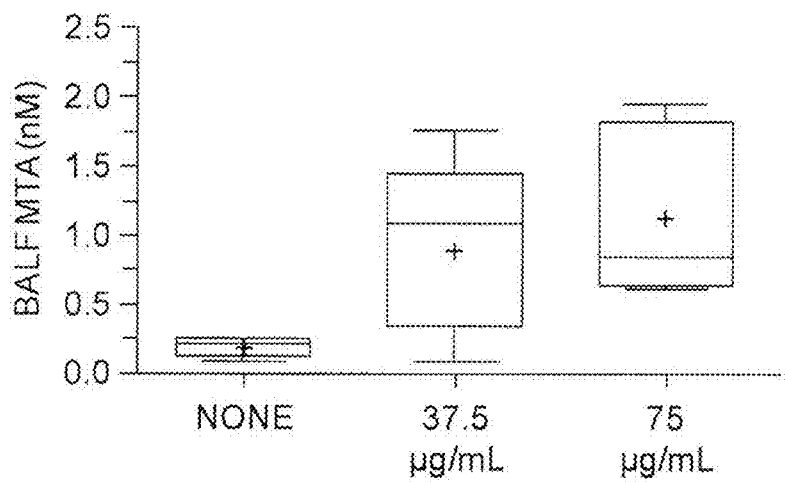

Previous studies have demonstrated that adding MTDIA to the drinking water can be an effective method for drug delivery that yields more consistent MTAP inhibition than once daily dosing. A concentration of MTDIA in drinking water that mimics the naturally occurring variations in MTA concentrations is determined, which our nasal lavage studies would suggest vary ~3-4 fold from those with low vs. high activity of the pathway (see FIG. 5). The effect of a range of MTDIA concentrations in drinking water on serum and BALF MTA concentrations in WT mice is explored using protocols similar to those described above, except that MTDIA is delivered in drinking water rather than oral gavage. In preliminary experiments, we calculated that 75 µg/mL of MTDIA in drinking water would deliver a dose of 15 mg/kg per day that we utilized in our single dose experiments (based on estimates of a 25 g mouse drinking 3 mL water per day), and we examined WT mice treated with this dose as well as half of this dose (37.5 µg/mL) relative to mice drinking untreated water. Using a MS method developed to measure MTDIA, we verified that drug is stable in drinking water over a three day time frame (FIG. 11A). Interestingly, in both the 37.5 and 75 µg/mL treatment groups, serum MTA concentrations were highly elevated, more than two orders of magnitude higher than control (FIG. 11B). Similar, though less dramatic increases were observed in BALF MTA as well (FIG. 11C). These levels are similar to what we observe in PK experiments shortly after dosing (see FIGS. 7A-7C) and are much higher than we would like to target for chronic experiments. Therefore, these experiments are repeated with lower concentrations of MTDIA (e.g., 0.5, 5, 15 µg/mL) to find a concentration that delivers no more than one order of magnitude increase in serum MTA. Once this dose is established, this dose is tested over three days in our Scnn1b-Tg and CF/Scnn1b-Tg mice to ensure that we observe similar effects in these models. If we do not, then we will consider retesting at a higher MTDIA concentration.

Once we have established the concentration of MTDIA in drinking water that yields a significant but relatively modest increase in serum MTA, this concentration is tested in a long term experiment in Scnn1b-Tg and CF/Scnn1b-Tg mice with WT controls. Mice are housed in cages containing MTDIA in drinking water or untreated water (n=6/group for each genotype). At the end of one week, animals have BALF, serum, and tissues harvested and tested as described above. If we observe significant effects on airway inflammation, these procedures are repeated on a mice week treated with two, four, and eight weeks of MTDIA (n=6/group). MS, cytokine, and inflammatory cell counts analyses are performed as described previously, and mice treated with drinking water alone are assessed as controls.

Oral treatment with MTDIA results in increases in both systemic (serum) and airway MTA concentrations that are associated with decreased airway inflammation. Systemic increases in MTA represent a potential source of toxicity, but we currently do not know if these systemic effects are also necessary for the reduction in airway inflammation. In light of these uncertainties, the possibility of developing inhaled MTDIA as a therapeutic option that will limit drug effects primarily to the airway is explored.

The pharmacokinetic (PK) and pharmacodynamic (PD) properties of airway administration of MTDIA via intra-tracheal administration in WT mice are determined. 20 µL of MTDIA in PBS is administered intratracheally, and BALF is collected at various time intervals post instillation in different groups of animals (n=3/group). For initial experiments, a range of concentrations of MTDIA (10, 100, 1000 µg/mL) is delivered as 20 µL intra-tracheal administration in WT mice (n=6/group). Mice are lavaged at a limited number of time points (15 min and 1 hr, n=3/group) to define the appropriate dosing range, with further experiments as needed based on the initial results. Drug PK and PD effects on MTA are measured by mass spectrometry. Once an optimal dose is established, a more extensive PK/PD analysis is performed using a greater number of time intervals (15 min, 30 min, 1 hr, 2 hr, 4 hr) in WT mice, then verified in Scnn1b-Tg and CF/Scnn1b-Tg mice. For these latter experiments, MTA, inflammatory cells, and cytokines are measured as described above. Depending on the results of these PK experiments, the ability of single dose airway administration of MTDIA to alter airway MTA concentrations and/or BALF cell counts at longer intervals after dosing is explored; e.g., by lavaging animals at 24 hr after dosing.

The foregoing is illustrative of the present invention, and is not to be construed as limiting thereof. The invention is defined by the following claims, with equivalents of the claims to be included therein.

That which is claimed is:

1. A method of inhibiting inflammation in the lungs of a subject having a lung disease associated with inflammation, comprising administering to the subject an effective amount of a transition state MTAP inhibitor, thereby inhibiting inflammation in the lungs of the subject;
   wherein the lung disease associated with inflammation is cystic fibrosis (CF), chronic obstructive pulmonary disorder (COPD), asthma, acute or chronic bronchitis, primary ciliary dyskinesia, bronchiectasis, acute respiratory distress syndrome, or any combination thereof; and
   wherein the MTAP inhibitor is:
   (a) methylthio-DADMe-Immucillin-A (MTDIA);
   (b) a compound of formula (I):

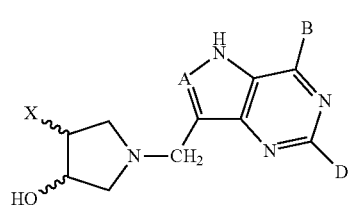

wherein

X is alkyl, cycloalkyl alkenyl, alkynyl, or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or $NR^2R^3$, wherein each alkylthio, arylthio and aralkylthio is optionally substituted with one or more alkyl, halogen, amino, hydroxy, or alkoxy, or X is SR1; or X is $NR^2R^3$;

$R^1$, $R^2$ and $R^3$ are independently selected from alkyl, alkenyl, alkynyl, aralkyl, or aryl, each of which is optionally substituted with one or more substituents selected from hydroxy, alkoxy, thiol, alkylthio, arylthio, aralkylthio, halogen, carboxylic acid, carboxylate alkyl ester, nitro, cyano or $NR^2R^3$, wherein each alkylthio, arylthio, and aralkylthio is optionally substituted with one or more alkyl halogen, amino, hydroxy, or alkoxy;

A is N or CH;

B is $NH_2$ or $NHR^4$;

$R^4$ is alkyl, alkenyl, alkynyl, aralkyl, aralkenyl, aralkynvl, or aryl, each of which is optionally substituted with one or more halogen or hydroxyl; and D is H, OH, $NH_2$, or $SCH_3$;

or a tautomer thereof, or a pharmaceutically acceptable salt thereof, or an ester prodrug form thereof;

provided that when B is $NH_2$, D is H and A is CH, X is not propyl, phenylethyl, $CH_2SQ$, $CH_2OH$, or $CH_2OQ$, wherein Q is optionally substituted alkyl, aralkyl, or aryl;

(c) a compound of formula (II):

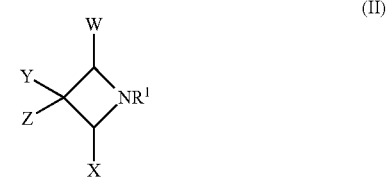

wherein

W and X are each independently selected from hydrogen, $CH_2OH$, $CH_2OQ$ and $CH_2SQ$;

Y and Z are each independently selected from hydrogen, halogen, $CH_2OH$, $CH_2OQ$, $CH_2SQ$, SQ, OQ and Q;

Q is alkyl, aralkyl, or aryl, each of which may be optionally substituted with one or more substituents selected from hydroxy, halogen, methoxy, amino, or carboxy;

$R^1$ is a radical of formula (III):

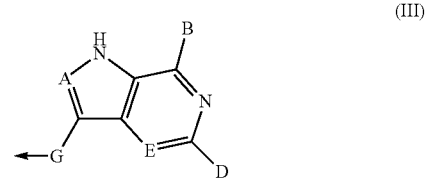

or $R^1$ is a radical of formula (IV):

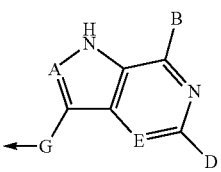

(IV)

A is selected from N, CH and CR²;
R² is selected from halogen, alkyl, aralkyl, aryl, OH, NH₂, NHR³, NR³R⁴ or SR⁵;
R³, R⁴, and R⁵ are each independently alkyl, aralkyl, or aryl optionally substituted with hydroxyl or halogen, and
wherein R² is optionally substituted with hydroxy or halogen when R² is alkyl, aralkyl or aryl;
B is selected from hydroxy, NH², NHR⁶, SH, hydrogen, or halogen;
R⁶ is alkyl, aralkyl, or aryl optionally substituted with hydroxy or halogen;
D is selected from hydroxy, NH₂, NHR⁷, hydrogen, halogen, or SCH₃;
R⁷ is alkyl, aralkyl, or awl group optionally substituted with hydroxy or halogen;
E is selected from N and CH;
G is C₁₋₄ saturated or unsaturated alkyl optionally substituted with hydroxy or halogen, or G is absent;
or a tautomer thereof, or a pharmaceutically acceptable salt thereof, or an ester thereof, or a prodrug thereof;
(d) a compound of formula (V):

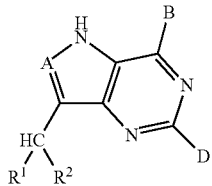

(V)

wherein
R¹ is H or NR³R⁴;
R² is H or alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or NR³R⁴, wherein each alkylthio, arylthio, and aralkylthio group is optionally substituted with one or more alkyl, halogen, amino, hydroxy, or alkoxy;
provided that when R¹ is H, R² is alkyl, alkenyl, alkynyl, aralkyl, aralkenyl, aralkynyl, or aryl which is substituted with at least one NR³R⁴;
R³ and R⁴, independently of each other, are H or is alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or NR³R⁴, wherein each alkylthio, arylthio and aralkylthio group is optionally substituted with one or more alkyl, halogen, amino, hydroxy, or alkoxy;
A is N or CH;
B is OH or alkoxy; and
D is H, OH, NH₂, or SCH₃;

provided that when R¹ is NR³R⁴, R² is H, A is CH, B is OH, and D is H, then R³ is not hydroxyethyl or hydroxypropyl when R⁴ is hydroxyethyl; and
provided that when R¹ is NR³R⁴, R² is H, A is CH, B is OH, and D is NH₂, then R³ is not hydroxyethyl when R⁴ is H, methyl, ethyl, or hydroxyethyl, and R⁴ is not hydroxyethyl when R³ is H, methyl, ethyl, or hydroxyethyl;
or a tautomer thereof, or a pharmaceutically acceptable salt thereof, or an ester prodrug form thereof; or
(e) a compound of formula (VI):

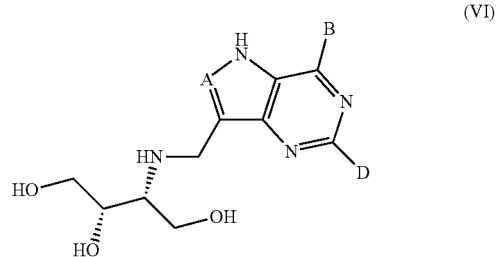

(VI)

where A is N or CH: B is OH or alkoxy; and D is H, OH, NH₂ or SCH₃.

2. The method of claim 1, wherein the MTAP inhibitor is administered after the onset of inflammation.

3. The method of claim 1, wherein the MTAP inhibitor is administered prior to the onset of inflammation.

4. The method of claim 1, wherein the lung disease associated with inflammation is CF and/or COPD.

5. A method of treating a lung disease associated with inflammation in a subject in need thereof, comprising administering to the subject a therapeutically effective amount of a transition state MTAP inhibitor, thereby treating the lung disease associated with inflammation in the subject;
wherein the lung disease associated with inflammation is cystic fibrosis, chronic obstructive pulmonary disorder, asthma, acute or chronic bronchitis, primary ciliary dyskinesia, bronchiectasis, acute respiratory distress syndrome, or any combination thereof; and
wherein the MTAP inhibitor is:
(a) methylthio-DADMe-Immucillin-A (MTDIA);
(b) a compound of formula (I):

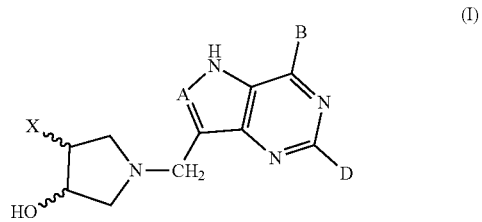

(I)

wherein
X is alkyl, cycloalkyl alkenyl, alkynyl, or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR²R³, wherein each alkylthio, arylthio and aralkylthio is optionally substituted with one or more alkyl, halogen, amino, hydroxy, or alkoxy; or
X is SR1; or X is $NR^2R^3$;

$R^1$, $R^2$ and $R^3$ are independently selected from alkyl, alkenyl, alkynyl, aralkyl, or aryl, each of which is optionally substituted with one or more substituents selected from hydroxy, alkoxy, thiol, alkylthio, arylthio, aralkylthio, halogen, carboxylic acid, carboxylate alkyl ester, nitro, cyano or $NR^2R^3$, wherein each alkylthio, arylthio, and aralkylthio is optionally substituted with one or more alkyl, halogen, amino, hydroxy, or alkoxy;

A is N or CH;

B is NH, or $NHR^4$;

$R^4$ is alkyl, alkenyl, alkynyl, aralkyl, aralkenyl, aralkynyl, or aryl, each of which is optionally substituted with one or more halogen or hydroxyl; and D is H, OH, $NH_2$, or $SCH_3$;

or a tautomer thereof, or a pharmaceutically acceptable salt thereof, or an ester prodrug form thereof;

provided that when B is $NH_2$, D is H and A is CH, X is not propyl, phenylethyl, $CH_2SQ$, $CH_2OH$, or $CH_2OQ$, wherein Q is optionally substituted alkyl, aralkyl, or aryl;

(c) a compound of formula (II):

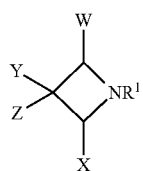

(II)

wherein

W and X are each independently selected from hydrogen, $CH_2OH$, $CH_2OQ$ and $CH_2SQ$;

Y and Z are each independently selected from hydrogen, halogen, $CH_2OH$, $CH_2OQ$, $CH_2SQ$, OQ and Q;

Q is alkyl, aralkyl, or aryl, each of which may be optionally substituted with one or more substituents selected from hydroxy, halogen, methoxy, amino, or carboxy;

$R^1$ is a radical of formula (III):

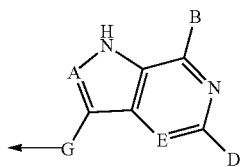

(III)

or $R^1$ is a radical of formula (IV):

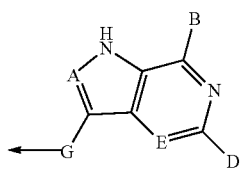

(IV)

A is selected from N, CH and $CR^2$;

$R^2$ is selected from halogen, alkyl, aralkyl, aryl, OH, $NH_2$, $NHR^3$, $NR^3R^4$ or $SR^5$;

$R^3$, $R^4$, and $R^5$ are each independently alkyl, aralkyl, or aryl optionally substituted with hydroxyl or halogen, and wherein $R^2$ is optionally substituted with hydroxy or halogen when $R^2$ is alkyl, aralkyl or aryl;

B is selected from hydroxy, $NH^2$, $NHR^6$, SH, hydrogen, or halogen;

$R^6$ is alkyl, aralkyl, or aryl optionally substituted with hydroxy or halogen;

D is selected from hydroxy, $NH_2$, $NHR^7$, hydrogen, halogen, or $SCH_3$;

$R^7$ is alkyl, aralkyl, or aryl group optionally substituted with hydroxy or halogen;

E is selected from N and CH;

G is $C_{1-4}$ saturated or unsaturated alkyl optionally substituted with hydroxy or halogen, or G is absent;

or a tautomer thereof, or a pharmaceutically acceptable salt thereof, or an ester thereof, or a prodrug thereof;

(d) a compound of formula (V):

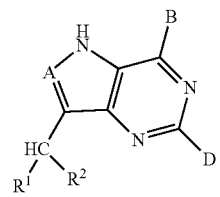

(V)

wherein $R^1$ is H or $NR^3R^4$;

$R^2$ is H or alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio group is optionally substituted with one or more alkyl, halogen, amino, hydroxy, or alkoxy;

provided that when $R^1$ is H, $R^2$ is alkyl, alkenyl, alkynyl, aralkyl, aralkenyl, aralkynyl, or aryl which is substituted with at least one $NR^3R^4$;

$R^3$ and $R^4$, independently of each other, are H or is alkyl, alkenyl, alkynyl, aralkyl, aralkenyl, aralkynvl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio and aralkylthio group is optionally substituted with one or more alkyl, halogen, amino, hydroxy, or alkoxy;

A is N or CH;

B is OH or alkoxy; and

D is H, OH, $NH_2$, or $SCH_3$;

provided that when $R^1$ is $NR^3R^4$, $R^2$ is H, A is CH, B is OH, and D is H, then $R^3$ is not hydroxyethyl or hydroxypropyl when $R^4$ is hydroxyethyl; and provided that when $R^1$ is $NR^3R^4$, $R^2$ is H, A is CH, B is OH, and D is $NH_2$, then $R^3$ is not hydroxyethyl when $R^4$ is H, methyl, ethyl, or hydroxyethyl, and $R^4$ is not hydroxyethyl when $R^3$ is H, methyl, ethyl, or hydroxyethyl;

or a tautomer thereof, or a pharmaceutically acceptable salt thereof, or an ester prodrug form thereof, or (e) a compound of formula (VI):

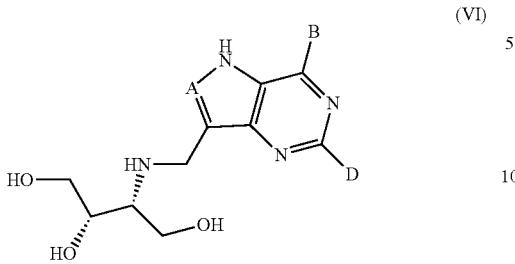

where A is N or CH; B is OH or alkoxy; and D is H, OH, NH$_2$, or SCH$_3$.

6. The method of claim 5, wherein the lung disease associated with inflammation is CF and/or COPD.

7. The method of claim 5, wherein the MTAP inhibitor is administered chronically.

8. The method of claim 5, wherein the MTAP inhibitor is administered at a time of pulmonary exacerbation.

9. The method of claim 5, further comprising administering to the subject a second agent for treatment of the lung disease associated with inflammation.

10. The method of claim 9, wherein the second agent is a bronchodilator, hypertonic saline solution, dornase alpha, an antibiotic, an anti-inflammatory agent, an antibacterial with anti-inflammatory properties, a modulator of intracellular signaling, an inhibitor of neutrophil influx, a CXCR2 antagonist, an anti-oxidant, an anti-protease, DMP-777, EPI-hNE4, a monocyte/neutrophil elastase inhibitor, a recombinant secretory leukoprotease inhibitor, lumacaftor, ivacaftor, a disulfide reducing agent, or any combination thereof.

11. The method of claim 5, wherein the MTAP inhibitor is administered intravenously, intraperitoneally, or by nasal and/or oral inhalation.

12. The method of claim 5, wherein the subject is a human.

13. The method of claim 5, wherein the selective MTAP inhibitor is methylthio-DADMe-Immucillin-A (MTDIA).

14. The method of claim 5, wherein the selective MTAP inhibitor is a compound of formula (I):

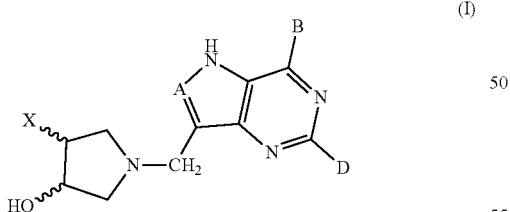

wherein
X is alkyl, cycloalkyl alkenyl, alkynyl, or aryl, each of which is optionally substituted with one or more substituents selected from hydroxy, alkoxy, cycloalkyl, thiol, alkylthio, arylthio, aralkylthio, halogen, carboxylic acid, carboxylate alkyl ester, nitro, cyano, thiazole, or NR$^2$R$^3$, wherein each alkylthio, arylthio and aralkylthio is optionally substituted with one or more alkyl, halogen, amino, hydroxy, or alkoxy; or
X is SR1; or
X is NR$^2$R$^3$;

R$^1$, R$^2$ and R$^3$ are independently selected from alkyl, alkenyl, alkynyl, aralkyl, or aryl, each of which is optionally substituted with one or more substituents selected from hydroxy, alkoxy, thiol, alkylthio, arylthio, aralkylthio, halogen, carboxylic acid, carboxylate alkyl ester, nitro, cyano or NR$^2$R$^3$, wherein each alkylthio, arylthio, and aralkylthio is optionally substituted with one or more alkyl, halogen, amino, hydroxy, or alkoxy;

A is N or CH;

B is NH$_2$ or NHR$^4$;

R$^4$ is alkyl, alkenyl, alkynyl, aralkyl, aralkenyl, aralkynyl, or aryl, each of which is optionally substituted with one or more halogen or hydroxyl; and D is H, OH, NH$_2$, or SCH$_3$;

or a tautomer thereof, or a pharmaceutically acceptable salt thereof, or an ester prodrug form thereof;

provided that when B is NH$_2$, D is H and A is CH, X is not propyl, phenylethyl, CH$_2$SQ, CH$_2$OH, or CH$_2$OQ, wherein Q is optionally substituted alkyl, aralkyl, or aryl.

15. The method of claim 14, wherein the selective MTAP inhibitor is a compound of formula (Ia):

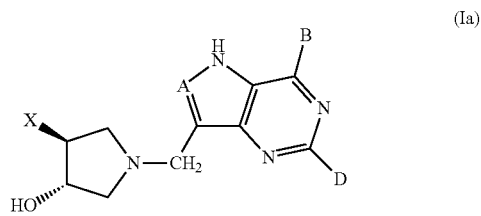

provided that when B is NH$_2$, D is H and A is CH, X is not propyl, phenylethyl, CH$_2$SQ, CH$_2$OH, or CH$_2$OQ, wherein Q is optionally substituted alkyl, aralkyl, or aryl;

or a tautomer thereof, or a pharmaceutically acceptable salt thereof, or an ester prodrug form thereof.

16. The method of claim 14, wherein the selective MTAP inhibitor is a compound of formula (Ib):

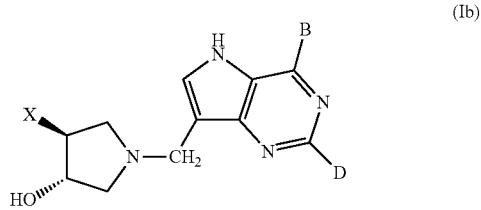

provided that X is not propyl, phenylethyl, CH2SQ, CH2OH or CH2OQ, where Q is an optionally substituted alkyl, aralkyl or aryl group, or a tautomer thereof, or a pharmaceutically acceptable salt thereof, or an ester prodrug form thereof.

17. The method of claim 5, wherein the selective MTAP inhibitor is a compound of formula (II):

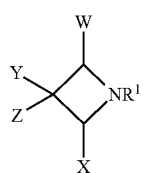
(II)

wherein
W and X are each independently selected from hydrogen, $CH_2OH$, $CH_2OQ$ and $CH_2SQ$;
Y and Z are each independently selected from hydrogen, halogen, $CH_2OH$, $CH_2OQ$, $CH_2SQ$, SQ, OQ and Q;
Q is alkyl, aralkyl, or aryl, each of which may be optionally substituted with one or more substituents selected from hydroxy, halogen, methoxy, amino, or carboxy;
$R^1$ is a radical of formula (III):

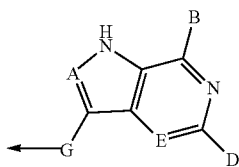
(III)

or
$R^1$ is a radical of formula (IV):

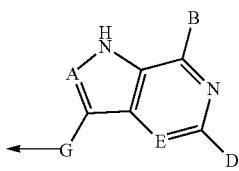
(IV)

A is selected from N, CH and $CR^2$;
$R^2$ is selected from halogen, alkyl, aralkyl, aryl, OH, $NH_2$, $NHR^3$, $NR^3R^4$ or $SR^5$;
$R^3$, $R^4$, and $R^5$ are each independently alkyl, aralkyl, or aryl optionally substituted with hydroxyl or halogen, and
wherein $R^2$ is optionally substituted with hydroxy or halogen when $R^2$ is alkyl, aralkyl or aryl;
B is selected from hydroxy, $NH_2$, $NHR^6$, SH, hydrogen, or halogen;
$R^6$ is alkyl, aralkyl, or aryl optionally substituted with hydroxy or halogen;
D is selected from hydroxy, $NH_2$, $NHR^7$, hydrogen, halogen, or $SCH_3$;
$R^7$ is alkyl, aralkyl, or aryl group optionally substituted with hydroxy or halogen;
E is selected from N and CH;
G is $C_{1-4}$ saturated or unsaturated alkyl optionally substituted with hydroxy or halogen, or G is absent;
or a tautomer thereof, or a pharmaceutically acceptable salt thereof, or an ester thereof, or a prodrug thereof.
18. The method of claim 5, wherein the selective MTAP inhibitor is a compound of formula (V):

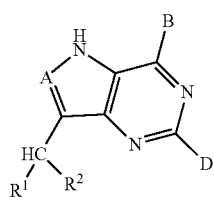
(V)

wherein
$R^1$ is H or $NR^3R^4$;
$R^2$ is H or alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio, and aralkylthio group is optionally substituted with one or more alkyl, halogen, amino, hydroxy, or alkoxy;
provided that when $R^1$ is H, $R^2$ is alkyl, alkenyl, alkynyl, aralkyl, aralkenyl, aralkynyl, or aryl which is substituted with at least one $NR^3R^4$;
$R^3$ and $R^4$, independently of each other, are H or is alkyl, alkenyl, alkynyl, aralkyl, aralkenyl, aralkynyl, or aryl each of which is optionally substituted with one or more hydroxy, alkoxy, thiol, alkylthio, arylthio, aralkylthio, halogen, carboxylic acid, carboxylate alkyl ester, nitro, or $NR^3R^4$, wherein each alkylthio, arylthio and aralkylthio group is optionally substituted with one or more alkyl, halogen, amino, hydroxy, or alkoxy;
A is N or CH;
B is OH or alkoxy; and
D is H, OH, $NH_2$, or $SCH_3$;
provided that when $R^1$ is $NR^3R^4$, $R^2$ is H, A is CH, B is OH, and D is H, then $R^3$ is not hydroxyethyl or hydroxypropyl when $R^4$ is hydroxyethyl; and
provided that when $R^1$ is $NR^3R^4$, $R^2$ is H, A is CH, B is OH, and D is $NH_2$, then $R^3$ is not hydroxyethyl when $R^4$ is H, methyl, ethyl, or hydroxyethyl, and $R^4$ is not hydroxyethyl when $R^3$ is H, methyl, ethyl, or hydroxyethyl;
or a tautomer thereof, or a pharmaceutically acceptable salt thereof, or an ester prodrug form thereof.
19. The method of claim 5, wherein the selective MTAP inhibitor is a compound of formula (VI):

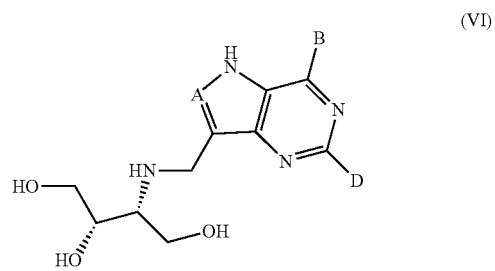
(VI)

where A is N or CH; B is OH or alkoxy; and D is H, OH, $NH_2$, or $SCH_3$.
20. The method of claim 1, wherein the selective MTAP inhibitor is a compound of formula (Ia):

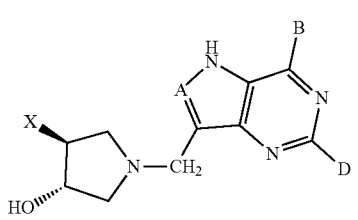

(Ia)

provided that when B is $NH_2$, D is H and A is CH, X is not propyl, phenylethyl, $CH_2SQ$, $CH_2OH$, or $CH_2OQ$, wherein Q is optionally substituted alkyl, aralkyl, or aryl;

or a tautomer thereof, or a pharmaceutically acceptable salt thereof, or an ester prodrug form thereof.

21. The method of claim 1, wherein the selective MTAP inhibitor is a compound of formula (Ib):

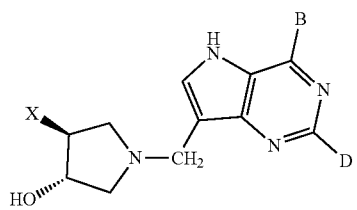

(Ib)

provided that X is not propyl, phenylethyl, CH2SQ, CH2OH or CH2OQ, where Q is an optionally substituted alkyl, aralkyl or aryl group, or a tautomer thereof, or a pharmaceutically acceptable salt thereof, or an ester prodrug form thereof.

* * * * *

UNITED STATES PATENT AND TRADEMARK OFFICE
CERTIFICATE OF CORRECTION

PATENT NO. : 10,918,641 B2
APPLICATION NO. : 15/943964
DATED : February 16, 2021
INVENTOR(S) : Esther, Jr. et al.

It is certified that error appears in the above-identified patent and that said Letters Patent is hereby corrected as shown below:

In the Specification

Column 5, Line 9: Please correct "+1%, +0.5%" to read -- ±1%, ±0.5% --

Column 29, Line 10: Please correct "86 μM" to read -- 86 pM --

Column 33, Line 64: Please correct "MIP-1a" to read -- MIP-1α --

In the Claims

Column 38, Line 23, Claim 1: Please correct "aralkynvl" to read -- aralkynyl --

Column 39, Line 25, Claim 1: Please correct "awl group" to read -- aryl group --

Column 41, Line 12, Claim 5: Please correct "B is NH," to read -- B is $NH_2$, --

Column 42, Line 48, Claim 5: Please correct "aralkynvl" to read -- aralkynyl --

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*